US010780144B2

(12) United States Patent
Bartizal et al.

(10) Patent No.: US 10,780,144 B2
(45) Date of Patent: *Sep. 22, 2020

(54) METHODS FOR PREVENTING AND TREATING PNEUMOCYSTIS INFECTIONS

(71) Applicant: Cidara Therapeutics, Inc., San Diego, CA (US)

(72) Inventors: Kenneth Bartizal, La Jolla, CA (US); Paul Daruwala, Del Mar, CA (US); Voon Ong, San Diego, CA (US); Maureen Roden, Severna Park, MD (US); Taylor Sandison, Encinitas, CA (US); Dirk Thye, San Diego, CA (US)

(73) Assignee: Cidara Therapeutics, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/529,390

(22) Filed: Aug. 1, 2019

(65) Prior Publication Data

US 2020/0164022 A1 May 28, 2020

Related U.S. Application Data

(63) Continuation of application No. 16/067,713, filed as application No. PCT/US2017/012533 on Jan. 6, 2017, now Pat. No. 10,369,188.

(60) Provisional application No. 62/350,577, filed on Jun. 15, 2016, provisional application No. 62/309,316, filed on Mar. 16, 2016, provisional application No. 62/276,370, filed on Jan. 8, 2016.

(51) Int. Cl.

| A61K 38/00 | (2006.01) |
|---|---|
| A61K 38/12 | (2006.01) |
| A61K 9/00 | (2006.01) |
| A61P 31/10 | (2006.01) |
| A61K 47/06 | (2006.01) |
| A61K 45/06 | (2006.01) |
| C07K 7/50 | (2006.01) |

(52) U.S. Cl.
CPC .............. *A61K 38/12* (2013.01); *A61K 9/007* (2013.01); *A61K 9/0019* (2013.01); *A61K 9/0053* (2013.01); *A61K 9/0073* (2013.01); *A61K 38/005* (2013.01); *A61K 45/06* (2013.01); *A61K 47/06* (2013.01); *A61P 31/10* (2018.01); *C07K 7/50* (2013.01)

(58) Field of Classification Search
None
See application file for complete search history.

(56) References Cited

U.S. PATENT DOCUMENTS

| 5,166,135 A | 11/1992 | Schmatz |
|---|---|---|
| 5,378,804 A | 1/1995 | Balkovec et al. |
| 5,399,552 A | 3/1995 | Bouffard |
| 5,514,651 A | 5/1996 | Balkovec et al. |
| 5,516,756 A | 5/1996 | Balkovec et al. |
| 5,541,160 A | 7/1996 | Balkovec et al. |
| 5,652,213 A | 7/1997 | Jamison et al. |
| 5,741,775 A | 4/1998 | Balkovec et al. |
| 5,854,213 A | 12/1998 | Bouffard |
| 5,948,753 A | 9/1999 | Balkovec et al. |
| 6,030,944 A | 2/2000 | Bouffard et al. |
| 6,069,126 A * | 5/2000 | Abruzzo ............... A61K 38/12 514/3.3 |
| 6,268,338 B1 | 7/2001 | Balkovec et al. |
| 6,506,726 B1 | 1/2003 | Dobbins et al. |
| 6,821,951 B2 | 11/2004 | Schwier et al. |
| 7,198,796 B2 | 4/2007 | Stogniew |
| 7,452,861 B2 | 11/2008 | Kaniga |
| 8,722,619 B2 | 5/2014 | James, Jr. et al. |
| 9,217,014 B2 | 12/2015 | James, Jr. et al. |
| 9,526,835 B2 | 12/2016 | Radhakrishnan et al. |
| 9,676,821 B2 | 6/2017 | James, Jr. et al. |
| 10,016,479 B2 | 7/2018 | Radhakrishnan et al. |
| 10,369,188 B2 | 8/2019 | Bartizal et al |
| 2004/0180965 A1 | 9/2004 | Borgman et al. |
| 2005/0026819 A1 | 2/2005 | Kaniga |
| 2005/0043222 A1 | 2/2005 | Lukacs et al. |
| 2006/0276339 A1 | 12/2006 | Windsor et al. |
| 2007/0231258 A1 | 10/2007 | Perakyla et al. |
| 2009/0074859 A1 | 3/2009 | Patel |
| 2009/0238867 A1 | 9/2009 | Jenkins et al. |
| 2010/0009009 A1 | 1/2010 | Young et al. |
| 2010/0075302 A1 | 3/2010 | Perlin et al. |
| 2013/0011452 A1 | 1/2013 | Loupenok |
| 2013/0150451 A1 | 6/2013 | Salamone et al. |
| 2013/0244930 A1 | 9/2013 | James, Jr. et al. |
| 2015/0024997 A1 | 1/2015 | James, Jr. et al. |
| 2015/0087583 A1 | 3/2015 | Radhakrishnan et al. |
| 2016/0045611 A1 | 2/2016 | Hecht et al. |
| 2016/0058717 A1 | 3/2016 | Page et al. |
| 2016/0075740 A1 | 3/2016 | James, Jr. et al. |
| 2016/0213742 A1 | 7/2016 | Forrest et al. |
| 2017/0151306 A1 | 6/2017 | Radhakrishnan et al. |
| 2017/0253635 A1 | 9/2017 | James, Jr. et al. |
| 2018/0256673 A1 | 9/2018 | Balkovec et al. |
| 2019/0000917 A1 | 1/2019 | Bartizal et al. |
| 2019/0160141 A1 | 5/2019 | Radhakrishnan et al. |

FOREIGN PATENT DOCUMENTS

| CN | 102766198 A | 11/2012 |
|---|---|---|
| CN | 103889221 A | 6/2014 |

(Continued)

OTHER PUBLICATIONS

Baskin et al. Organic Process Research & Development 2000, 4, 427-435.*

(Continued)

*Primary Examiner* — Jeanette M Lieb
(74) *Attorney, Agent, or Firm* — Clark & Elbing LLP

(57) ABSTRACT

The disclosure relates to methods of prophylactic and therapeutic treatments of a *Pneumocystis* infection (i.e., an infection caused by *Pneumocystis jirovecii*) in a subject by administering to the subject a compound of any of formulas (I)-(III) (e.g., a salt of Compound 1, or a neutral form thereof). The disclosure also relates to methods of inhibiting the replication of a *Pneumocystis* spp. The methods of the disclosure can be useful in immunocompromised subjects.

17 Claims, 9 Drawing Sheets

(56) References Cited

FOREIGN PATENT DOCUMENTS

| | | |
|---|---|---|
| JP | 2014-516339 A | 7/2014 |
| JP | 2015-512392 A | 4/2015 |
| WO | WO-96/08507 A1 | 3/1996 |
| WO | WO-2005/018743 A1 | 3/2005 |
| WO | WO-2008/093060 A2 | 8/2008 |
| WO | WO-2010/032011 A2 | 3/2010 |
| WO | WO-2010/128096 A1 | 11/2010 |
| WO | WO-2011/025875 A1 | 3/2011 |
| WO | WO-2011/089214 A1 | 7/2011 |
| WO | WO-2012/119065 A2 | 9/2012 |
| WO | WO-2013/017691 A1 | 2/2013 |
| WO | WO-2013/142279 A1 | 9/2013 |
| WO | WO-2014/113693 A1 | 7/2014 |
| WO | WO-2014/124504 A1 | 8/2014 |
| WO | WO-2015/035102 A2 | 3/2015 |
| WO | WO-2017/049102 A1 | 3/2017 |
| WO | WO-2017/049105 A1 | 3/2017 |
| WO | WO-2017/120471 A1 | 7/2017 |
| WO | WO-2017/161016 A1 | 9/2017 |
| WO | WO-2018/085200 A1 | 5/2018 |
| WO | WO-2018/102407 A1 | 6/2018 |
| WO | WO-2018/144600 A1 | 8/2018 |
| WO | WO-2018/187574 A1 | 10/2018 |
| WO | WO-2018/191692 A1 | 10/2018 |
| WO | WO-2018/014333 A1 | 1/2019 |
| WO | WO-2019/027498 A1 | 2/2019 |

OTHER PUBLICATIONS

"Echinocandin Dosing: An Opportunity for Improvement," Institute for Clinical Pharmacodynamics Presentation (2017) (82 pages).
"New Hope for Serious Infections," Cidara Therapeutics Corporate Presentation (2017) (39 pages).
Barrett, "From natural products to clinically useful antifungals," Biochim Biophys Acta. 1587(2-3):224-33 (2002).
Boikov et al., "In vitro activity of the novel echinocandin CD101 at pH 7 and 4 against *Candida* spp. isolates from patients with vulvovaginal candidiasis," J Antimicrob Chemother. 72(5):1355-8 (2017).
Bouffard et al., "Synthesis and antifungal activity of novel cationic pneumocandin Bo derivatives," J Med Chem. 37(2): 222-5 (1994).
Chandra et al., "Evaluate the Ability of CD101 to Prevent and Treat Candida albicaris Biofilms and Explore its Temporal Effect by Time Lapse Photography," 8th Trends in Medical Mycology, Oct. 6-9, Belgrade, Serbia. Abstract Poster No. P057 (2017).
Chatterjee et al., "Draft genome of a commonly misdiagnosed muitidrug resistant pathogen *Candida auris*," BMC Genomics. 16:686 (2015) (16 pages).
Communication pursuant to Article 94(3) EPC for European Patent Application No. 13764974.5, dated Nov. 18, 2016 (4 pages).
Crandon et al., "Bronchopulmoriary disposition of intravenous voriconazole and anidulatungin given in combination to healthy adults," Antimicrob Agents Chemother. 53(12):5102-7 (2009).
Cuenca-Estrella et al., "Susceptibility of fluconazole-resistant clinical isolates of *Candida* spp. to echinocandin LY303366, itraconazole and amphotericin B," J Antimicrob Chemother. 46(3): 475-7 (2000).
Cushion et al., "Echinocandin treatment of *Pneumocystis* pneumonia in rodent models depletes cysts leaving trophic burdens that cannot transmit the infection," PLoS One. 5(1):e8524 (2010) (12 pages).
Cushion et al., "Efficacy of CD101, a novel Echinocandin, in prevention of *Pneumocytsis* Pneumonia (PCP): thwarting the biphasic life cycle of *Pneumocystis*," Annual Meeting of the American Society of Hematology, Dec. 3-6, San Diego, California, Abstract 3396. Blood. 128(22) (2016) (1 page).
Cushion et al., "Novel Once-Weekly Echinocandin Rezafurigin (CD101) for Prevention and Treatment of Pneumocystis Biofilms," European Society for Blood and Marrow Transplantation (EBMT) Annual Meeting, Mar. 18-21, Lisbon, Portugal, Poster, (2018) (1 page).

Cushion et al., "Prevention of Pneumocystis Pneumonia (PCP) by the novel Echinocandin, CD101," American Society for Microbiology Microbe 2016, Jun. 17, 2016 (17 pages).
Denning et al., "Infectious Disease. How to bolster the antifungal pipeline," Science. 347(6229):1414-6 (2015) (4 pages).
Denning, "Echinocandin antifungal drugs," Lancet. 362(9390):1142-51 (2003).
Notice of Reasons for Rejection for Japanese Application No. 2018-036159, dated Nov. 12, 2019 (5 pages).
English translation of Office Action for Japanese Patent Application No. 2013-556894, dated Apr. 21, 2015 (2 pages).
English translation of Search Report for Chinese Application No. 201280021321.9, dated Jan. 6, 2015 (7 pages).
Espinel-Ingroff, "Comparison of in vitro activities of the new triazole SCH56592 and the echinocandins MK-0991 (L-743,872) and LY303366 against opportunistic filamentous and dimorphic fungi and yeasts," J Clin Microbiol. 36(10): 2950-6 (1998).
International Search Report and Written Opinion for International Application No. PCT/US2012/027451, dated Jun. 20, 2012 (16 pages).
International Search Report and Written Opinion for International Application No. PCT/US2013/031678, dated Jun. 12, 2013 (19 pages).
International Search Report and Written Opinion for International Application No. PCT/US2016/052159, dated Jan. 13, 2017 (16 pages).
International Search Report and Written Opinion for International Application No. PCT/US2016/052165, dated Jan. 9, 2017 (25 pages).
International Search Report and Written Opinion for International Application No. PCT/US2017/012533, dated May 8, 2017 (15 pages).
International Search Report and Written Opinion for International Application No. PCT/US2017/022551, dated Jun. 12, 2017 (15 pages).
International Search Report and Written Opinion for International Application No. PCT/US2017/059046, dated Apr. 3, 2018 (14 pages).
International Search Report and Written Opinion for International Application No. PCT/US2017/063696, dated Feb. 1, 2018 (14 pages).
International Search Report and Written Opinion for International Application No. PCT/US2018/014883, dated Mar. 29, 2018 (16 pages).
International Search Report and Written Opinion for International Application No. PCT/US2018/016236, dated May 2, 2018 (13 pages).
International Search Report and Written Opinion for International Application No. PCT/US2018/026261, dated Jul. 20, 2018 (15 pages).
International Search Report and Written Opinion for International Application No. PCT/US2018/027614, dated Jun. 29, 2018 (16 pages).
Invitation to Pay Additional Fees for International Application No. PCT/US2018/041617, dated Sep. 14, 2018 (2 pages).
James et al., "Biafungin (CD101), a novel echinocandin, displays a long half-life in the chimpanzee, suggesting a once-weekly IV dosing option," 54th Interscience Conference on Antimicrobial Agents and Chemotherapy, Sep. 5-9, Washington D.C., Abstract A-694, retrieved from <http://n33px2pjph02hfyxt1xmwn4m.wpengine.netdna-cdn.com/wp-content/uploads/2014/12/A-694.-Biafungin-CD101-a-Novel-Echinocandin-Displays-a-Long-Half-life-in-the-Chimpanzee-Suggesting-a-Once-Weekly-IV-Dosing-Option.pdf> (2014) (2 pages).
James et al., "Structure-Activity Relationships of a Series of Echinocandins and the Discovery of CD101, a Highly Stable and Soluble Echinocandin with Distinctive Pharmacokinetic Properties," Antimicrob Accents Chemother, 61(2):e01541-16 (2017) (8 pages).
Jamison et al., "The synthesis and antifungal activity of nitrogen containing herniaminal ethers of LY303366," J Antibiot (Tokyo). 51(2): 239-42 (1998).

(56) References Cited

OTHER PUBLICATIONS

Krishnan et al., "CD101, a novel echinocandin with exceptional stability properties and enhanced aqueous solubility," J Antibiot (Tokyo). 70(2):130-5 (2017).
Lakota et al., "Pharmacokinetic-Pharmacodynamic Target Attainment Analyses to Support the Selection of Extended-Interval CD101 Dosing Regimens," IDWeek 2016, Oct. 26-30, New Orleans, Louisiana. Poster No. 1994 (2016) (2 pages).
Locke et al., "Characterization of In Vitro Resistance Development to the Novel Echinocandin CD101 in *Candida* Species," Antirnicrob Agents Chemother, 60(10):6100-6107 (2016).
Metzler et al., "Comparison of minimal inhibitory and mutant prevention drug concentrations of 4 fluoroquinolones against clinical isolates of methicillin-susceptible and -resistant *Staphylococcus aureus*," Int J Antimicrob Agents, 24(2):161-7 (2004).
Office Action and English Translation for Chinese Application No. 201280021321.9, dated Nov. 16, 2015 (20 pages).
Office Action and English translation for Chinese Patent Application 201380026168.3, dated Sep. 15, 2015 (20 pages).
Office Action and English Translation for Russian Patent Application No. 201728118, dated Jun. 17, 2019 (8 pages).
Office Action for U.S. Appl. No. 15/371,333, dated Sep. 29, 2017 (23 pages).
Ong et al., "A Single-Dose, Subcutaneous (SC) Prophylaxis CD101 Administration Prevents Fungal Infection in Mouse Models of Candidiasis and Aspergillosis," ASM Microbe, Jun. 1-5, New Orleans, Louisiana, Poster 241 (2017).
Ong et al., "Antifungal Prophylaxis with CD101 in Immunosuppressed Mouse Models of Candidiasis, Aspergillosis, and Pneumocystis Pneumonia (PCP)," European Hematology Association Congress, Jun. 22-25, Madrid, Spain, Poster P645 (2017).
Ong et al., "Efficacy of CD101, a Novel Echinocandin, in Mouse Models of Aspergillosis and Azole-Resistant Disseminated Candidiasis," ASH Annual Meeting, Dec. 3-6, San Diego, California, 3400 (2016).
Ong et al., "Pharmacokinetics of the Novel Echinocandin CD101 in Multiple Animal Species," Antimicrob Agents Chemother. 61(4):e01626-16 (2017) (8 pages).
Ong et al., "Preclinical Evaluation of the Stability, Safety, and Efficacy of CD101, a Novel Echinocandin," Antimicrob Agents Chemother. 60(11):6872-9 (2016).
Ong et al., "Prophylactic, Single-Dose, Subcutaneous (SC) Administration of CD101 Shows Robust Efficacy in Neutropenic Mouse Models of Candidiasis and Aspergillosis," European Congress of Clinical Microbiology and Infectious Diseases, Apr. 22-25, Vienna, Austria, EP0703 (2017).
Ong et al., "Subcutaneous (SC) Injection of CD101, a Novel Echinocandin: Efficacious, Well-Tolerated and Sustained Drug Exposures," International Immunocompromised Host Society—Infocus, Nov. 13-15, Santiago, Chile, poster (2016).
Partial supplementary European Search Report for European Patent Application No. 12751994.0, dated Mar. 10, 2015 (5 pages).
Pfaller et al., "Activity of a Long-Acting Echinocandin (CD101) and Seven Comparator Antifungal Agents Tested against a Global Collection of Contemporary Invasive Fungal Isolates in the SENTRY 2014 Antifungal Surveillance Program," Antimicrob Agents Chemother. 61(3):e02045-16 (2017) (7 pages).
Pfailer et al., "Activity of a long-acting echinocandin, CD101, determined using CLSI and EUCAST reference methods, against *Candida* and *Aspergillus* spp., including echinocandin- and azole-resistant isolates," J Antimicrob Chemother. 71(10):2868-73 (2016).
Pfaller et al., "CD101, a long-acting echinocandin, and comparator antifungal agents tested against a global collection of invasive fungal isolates in the SENTRY 2015 Antifungal Surveillance Program," Int Journ Antimicrob Agents. 50(3):352-358 (2017).
Pfizer Inc., "Eraxis (anidulafungin) for Injection," <http://dailymed.nlm.nih.gov/dailymed/archives/fdaDrugInfo.cfm?archiveid=4744>, revised May 2007, retrieved on Oct. 1, 2015 (21 pages).
PubChem: Substance Record for SID 144216468, available Oct. 8, 2012, retrieved Feb. 9, 2017 (5 pages).
Rodriguez et al., "The Synthesis of Water Soluble Prodrugs Analogs of Echinocandin B," Bioorg Med Chem Lett. 9(13):1863-1868 (1999).
Sandison et al., "Pharmacokinetics, Safety, and Target Attainment of Single and Multiple Doses of CD101 IV—a Novel, Once-Weekly Echinocandin," 58th Annual Meeting of the American Society of Hematology, Dec. 5-8, San Diego, California. Abstract 2197 (2016) (1 page).
Sandison et al., "Safety arid Pharmacokinetics of CD101 IV, a Novel Echinocandin, in Healthy Adults," Antimicrob Agents Chemother, 61(2):e01627-16 (2017) (11 pages).
Sandison et al., "Safety and Pharmacokinetics of Multiple Doses of CD101 IV: Results From a Phase 1, Dose-Escalation Study," ASM Microbe 2016, Jun. 16-20, Boston, Massachusetts. Abstract LB-057 (2016) (1 page).
Sandison et al., "Safety and Pharmacokinetics of Single and Multiple Doses of CD101 IV: Results from Two Phase 1 Dose-Escalation Studies," 19th Immunocompromised Host Society Symposium, 14th Forum on Fungal Infection in the Clinical Practice, Nov. 13-15, Santiago, Chile (2016) (1 page).
Sandison et al., "Safety and Pharmacokinetics of Single and Multiple Doses of CD101 IV: Results from Two Phase 1 Dose-Escalation Studies," 2016 American College of Clinical Pharmacy Annual Meeting, Oct. 23-26, Hollywood, Florida. Poster 258 (2016) (1 page).
Sandison, "CD101: A Novel Echinocandin," Trends in Medical Mycology, Oct. 6-9, Belgrade, Serbia, presentation (2017) (16 pages).
Strickley, "Solubilizing excipients in oral and injectable formulations," Pharm Res. 21(2):201-30 (2004).
Thye, "The safety and single-dose pharmacokinetics of CD101 IV: results from a phase 1, dose-escalation study," 26th European Congress of Clinical Microbiology and Infectious Diseases, Amsterdam, Netherlands, Apr. 9-12, 2016. Retrieved from <http://www.cidara.com/wp-content/uploads/2016/04/The-safety-and-single-dose-pharmacokinetics-of-CD101-IV-results-from-a-phase-1-dose-escalation-study.pdf> (12 pages).
Uzun et al., "In vitro activity of a new echinocandin, LY303366, compared with those of amphotericin B and fluconazole against clinical yeast isolates," Antimicrob Agents Chemother. 41(5): 1156-7 (1997).
Verweij et al., "Efficacy of LY303366 against amphotericin B-susceptible and -resistant *Aspergillus furnigatus* in a murine model of invasive aspergillosis," Antimicrob Agents Chemother. 42(4): 873-78 (1998).
Walpole et al., "The weight of nations: an estimation of adult human biomass," BMC Public Health, 12:439 (2012) (6 pages).
Zhao et al., "CD101: a novel long-acting echinocandin," Cell Microbiol. 18(9):1308-16 (2016).
Zhao et al., "Unraveling Drug Penetration of Echinocandin Antifungals at the Site of Infection in an Intra-abdominal Abscess Model," Antimicrob Agents Chemother. 61(10):e01009-17 (2017) (13 pages).
Zimbeck et al., "FKS mutations and elevated echinocandin MIC values among Candida glabrata isolates from U.S. population-based surveillance," Antimicrob Agents Chemother. 54(12):5042-47 (2010).
Extended European Search Report for European Application No. 13764974.5, dated Oct. 26, 2015 (7 pages).
Extended European Search Report for International Patent Application No. 12751994.0, dated Jul. 27, 2015 (8 pages).
Fujie et al., "FR131535, a novel water-soluble echinocandin-like lipopeptide: synthesis and biological properties," Bioorg Med Chem Lett. 11(3):399-402 (2001).
Garcia-Effron et al., "Effect of Candida glabrata FKS1 and FKS2 mutations on echinocandin sensitivity and kinetics of 1,3-beta-D-glucan synthase: implication for the existing susceptibility breakpoint," Antimicrob Agents Chemother. 53(9):3690-3699 (2009).
Guo et al., "Synthesis and antifungal activities of glycosylated derivatives of the cyclic peptide fungicide caspofungin," ChemMedChem. 7(8):1496-503 (2012).
Heikkilä et al., "The prevalence of onychomycosis in Finland," Br J Dermatol. 133(5):699-703 (1995).

(56) References Cited

OTHER PUBLICATIONS

International Preliminary Report on Patentability for International Application No. PCT/US2013/031678, dated Sep. 23, 2014 (11 pages).
International Preliminary Report on Patentability for International Application No. PCT/US2017/022551, dated Sep. 27, 2018 (9 pages).
International Preliminary Report on Patentability for International Patent Application No. PCT/US2012/027451, dated Jan. 28, 2014 (7 pages).
International Search Report and Written Opinion for International Application No. PCT/US18/41617, dated Nov. 9, 2018 (16 pages).

\* cited by examiner

Compound 4

Compound 5

Compound 6

Compound 7

Compound 8

Compound 9

Compound 18

Compound 17

Compound 16

Compound 19

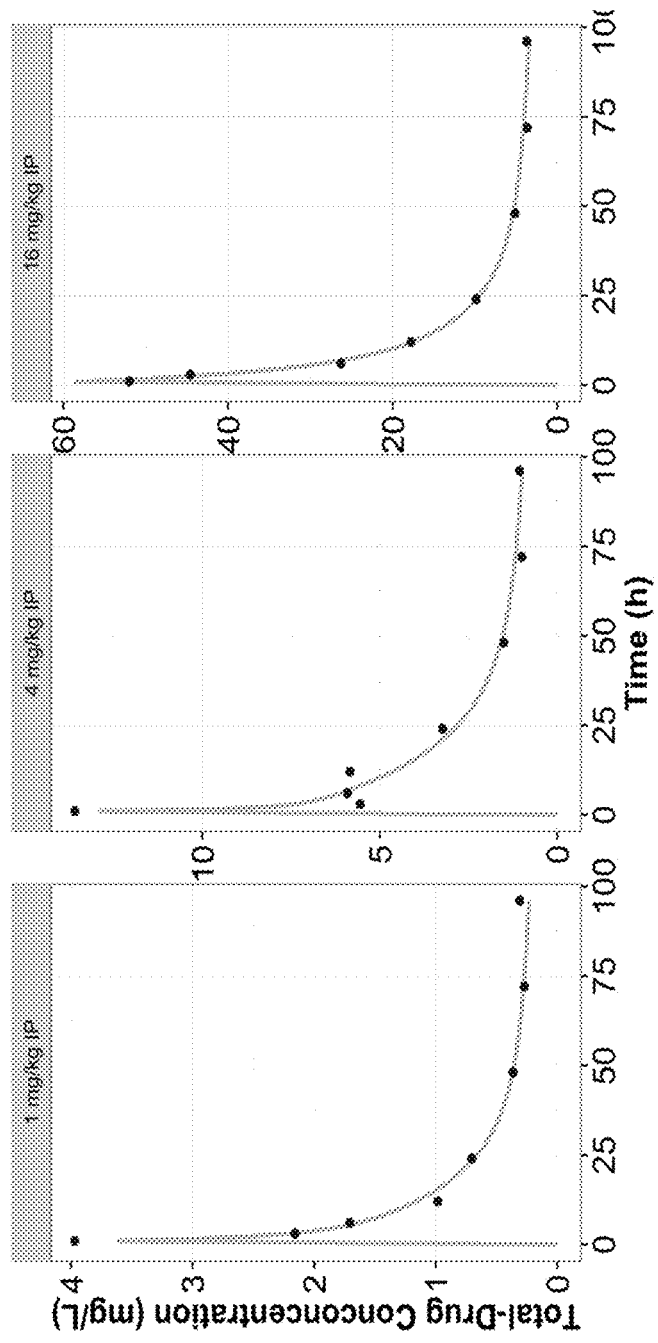
FIG. 4 Observed (solid circles) and model fitted (lines) Compound 1 concentrations versus time following administration of single Compound 1 doses)

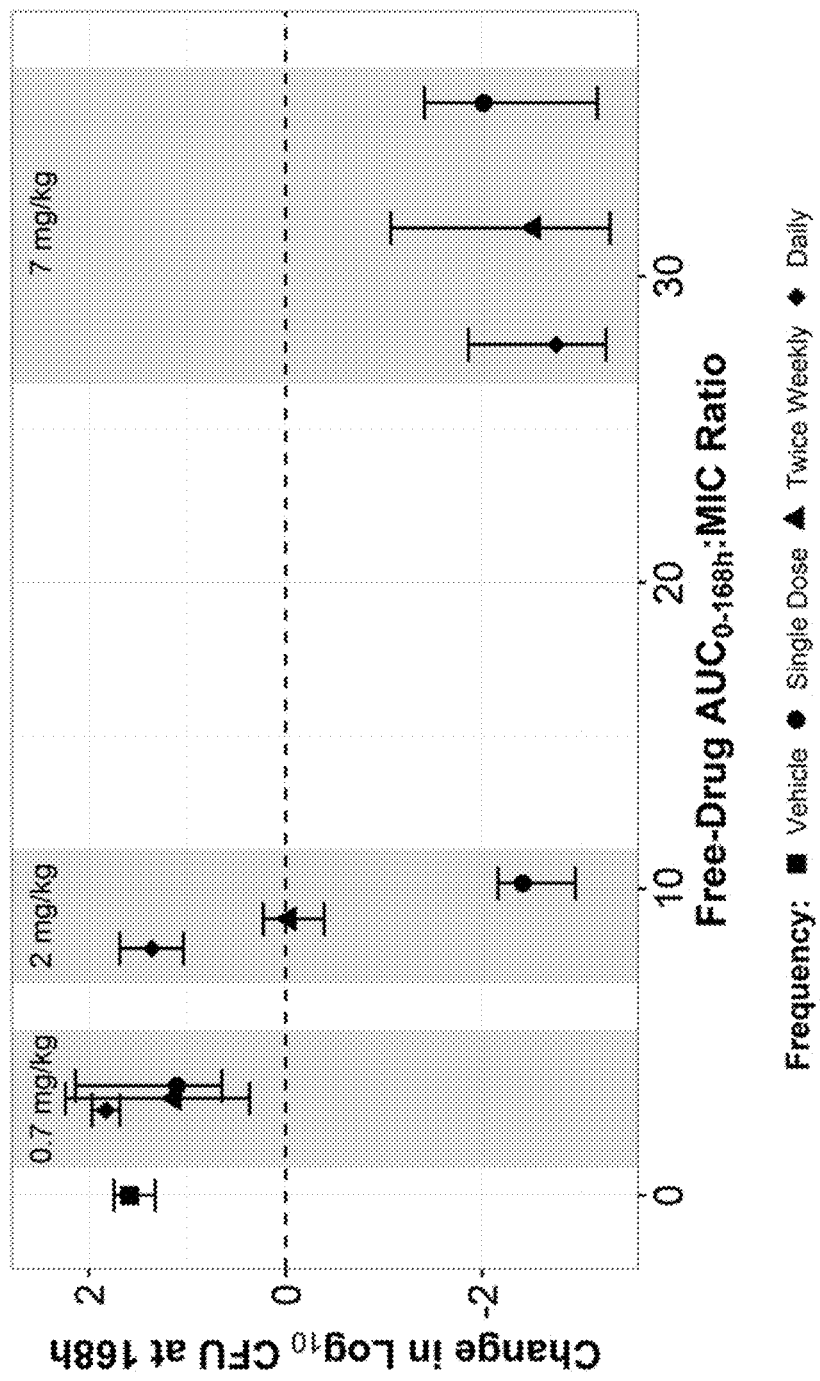
FIG. 5 Mean (solid circles) and range (error bars) change in $\log_{10}$ CFU from baseline versus $AUC_{0-168h}$:MIC ratio by fractionation schedule

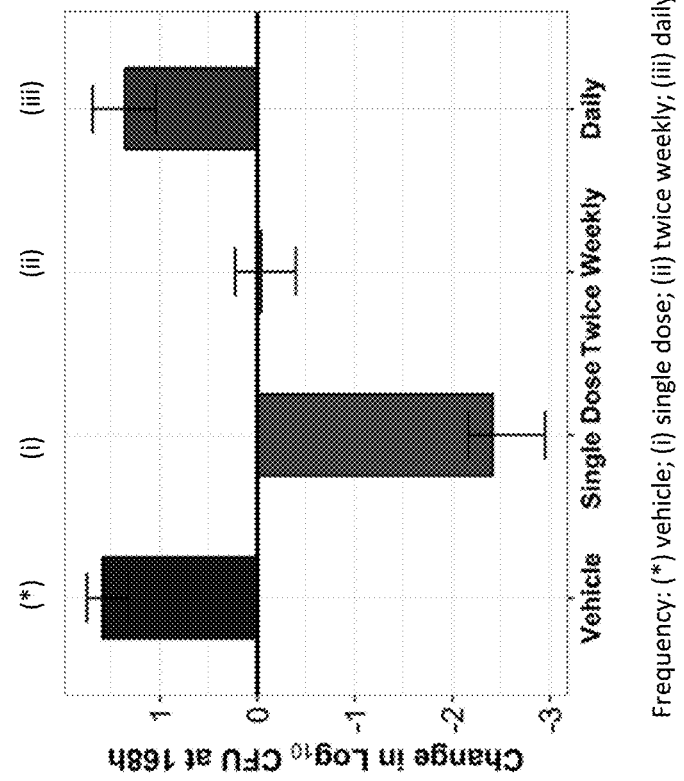
FIG. 6 Mean (bar) and range (error bars) change in $\log_{10}$ CFU from baseline allowing administration of Compound 1 2 mg/kg grouped by fractionation schedule
Frequency: (*) vehicle; (i) single dose; (ii) twice weekly; (iii) daily

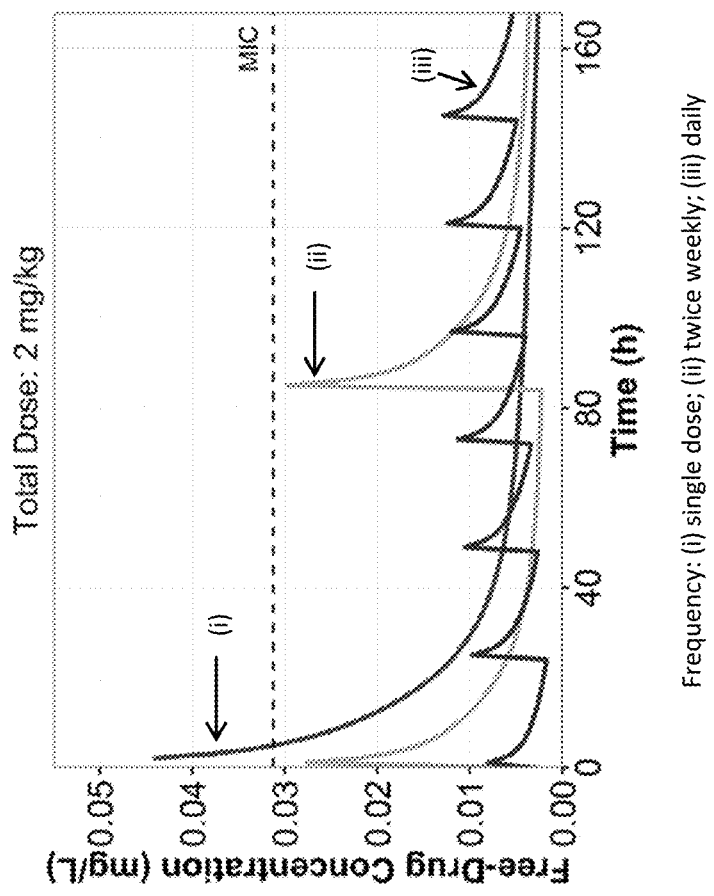
FIG. 7 Simulated free-drug concentration time profiles relative to the MIC for the fractionated Compound 1 2 mg/kg regimen

METHODS FOR PREVENTING AND TREATING PNEUMOCYSTIS INFECTIONS

BACKGROUND

*Pneumocystis* spp. are opportunistic pathogenic fungi that cause *Pneumocystis* infections (e.g., *pneumocystis* pneumonia (PCP)) in mammalian hosts with compromised immune systems. PCP is not responsive to standard antifungal therapy and there are few treatment alternatives. There is a need in the art for methods of preventing and treating *Pneumocystis* infections.

SUMMARY

The disclosure features methods for treating a *Pneumocystis* infection (e.g., an infection caused by *Pneumocystis jirovecii* in humans) or reducing the risk of a *Pneumocystis* infection in a subject (e.g., a human) in need thereof by administering to the subject a compound of any one of formulas (I)-(III) (e.g., a salt of Compound 1, or a neutral form thereof). In some embodiments, the subject is immunocompromised, and thus, especially vulnerable to *Pneumocystis* infections. The disclosure also features methods of inhibiting the replication of a *Pneumocystis* spp.

In a first aspect, the disclosure features a method of treating a *Pneumocystis* infection in a subject (e.g., a human), wherein the method includes administering to the subject in an amount and for a duration sufficient to treat the *Pneumocystis* infection a compound of any of formulas (I)-(III). In some embodiments, the treating includes reducing the cyst burden in the lung of the subject. In other embodiments, the treating includes inhibiting the reproduction of a *Pneumocystis* spp. in the subject. In particular embodiments, the subject being treated has *Pneumocystis* pneumonia.

In any of the above methods, the compound can be administered intraorally, intravenously, intramuscularly, intradermally, intraarterially, subcutaneously, orally, or by inhalation. In some embodiments, the compound is administered intravenously. In some embodiments, the compound is administered by inhalation. In some embodiments, the compound is administered orally. In certain embodiments, the subject is a human and the *Pneumocystis* infection is caused by *Pneumocystis jirovecii*.

In a second aspect, the disclosure features a method of reducing the risk of a *Pneumocystis* infection in a subject (e.g., a human) in need thereof, wherein the method includes administering to the subject in an amount and for a duration sufficient to reduce the risk of the *Pneumocystis* infection a compound of any of formulas (I)-(III).

In another embodiment of any of the above methods, the subject is immunocompromised. For example, the methods of the disclosure can be used to treat or reduce the risk of a *Pneumocystis* infection in a subject that is HIV positive or has hyper IgM syndrome. In one particular embodiment, the immunocompromised subject has a $CD4^+$ T-cell count of less than 200 cells/µl of blood. In still other embodiments, the compound of any of formulas (I)-(III), or a pharmaceutically acceptable salt thereof, is administered concurrently or within 7 days, 5 days, 3 days, or 1 day, before and/or after, the subject undergoes immunosuppression therapy. For example, the compound of any of formulas (I)-(III), or a pharmaceutically acceptable salt thereof, can be administered concurrently or within 7 days, 5 days, 3 days, or 1 day, before and/or after, the subject undergoes an anti-TNF therapy, a corticosteroid therapy, a chemotherapy, or any other treatment regimen or procedure associated with, or accompanied by, a suppressed immune system. In particular embodiments, the compound of any of formulas (I)-(III), or a pharmaceutically acceptable salt thereof, is administered concurrently or within 7 days, 5 days, 3 days, or 1 day, before and/or after, the subject undergoes a transplantation procedure. The transplantation procedure can be an organ transplant (e.g., a solid organ transplant) or a bone marrow transplant.

In any of the above methods, the compound of any of formulas (I)-(III), or a pharmaceutically acceptable salt thereof, can be administered concurrently with a second antifungal agent. In some embodiments, the second antifungal agent is clindamycin, trimethoprim, sulfamethoxazole, cotrimoxazole, atovaquone, pentamidine, primaquine, pyrimethamine, or a pharmaceutically acceptable salt thereof. In other embodiments, the second antifungal agent is selected from glucan synthase inhibitors, polyene compounds, azole compounds, and pharmaceutically acceptable salts thereof. For example, the second antifungal agent can be any glucan synthase inhibitor, polyene compound, or azole compound described herein.

In a third aspect, the disclosure features a method of inhibiting the replication of a *Pneumocystis* spp., wherein the method includes contacting the *Pneumocystis* spp., in an amount and for a duration sufficient to inhibit replication of the *Pneumocystis* spp., with a compound of any of formulas (I)-(III). In some embodiments, the *Pneumocystis* spp. is *Pneumocystis jirovecii*.

The structures of compounds of formulas (I)-(III) are shown below:

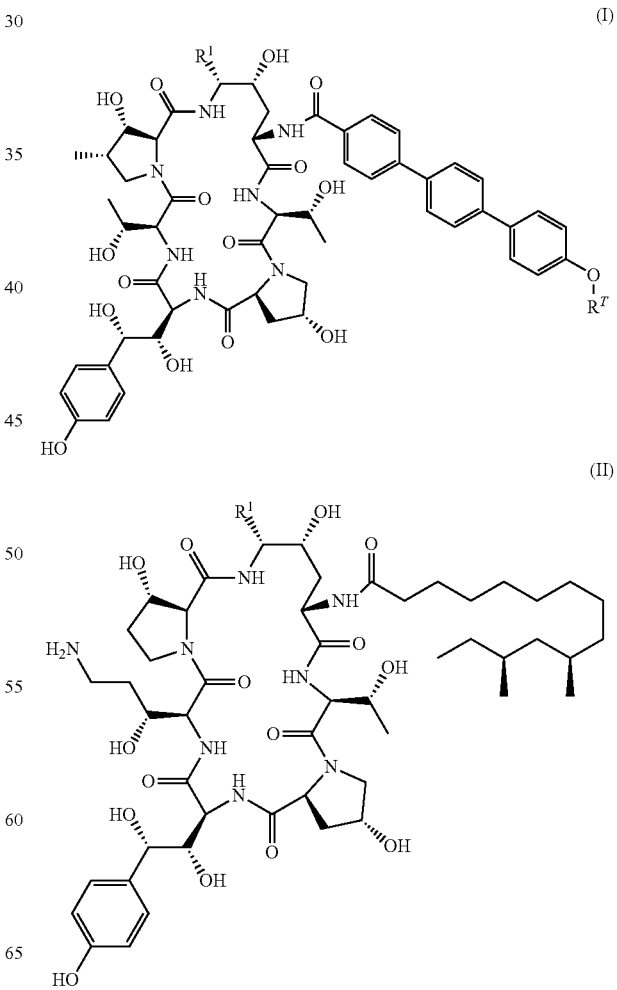

(III)

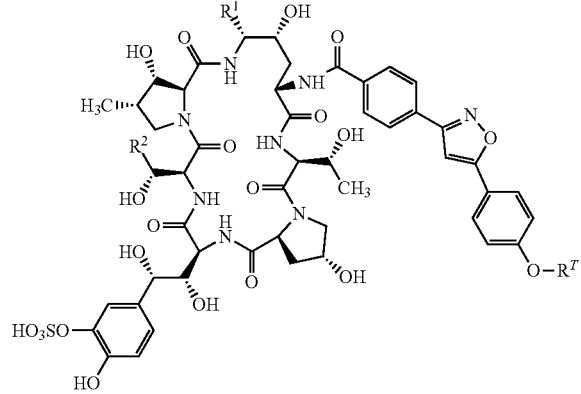

wherein $R^1$ is $O(CH_2CH_2O)_nCH_2CH_2X_1$, $O(CH_2CH_2NH)_n CH_2CH_2X_1$, $O(CH_2CH_2CH_2O)_nCH_2CH_2X_1$, $NHCH_2CH_2X_2$, $NH(CH_2CH_2O)_mCH_2CH_2X_2$, $NH(CH_2CH_2CH_2O)_mCH_2CH_2X_2$, $NH(CH_2CH_2O)_p CH_2CH_2X_3$, $NH(CH_2CH_2CH_2O)_pCH_2CH_2X_3$, $NHCH_2CH_2X_4$, $NH[CH_2(CH_2)_aO]_bCH\{CH_2[OCH_2(CH_2)_c]_d X_5\}_2$, $O[CH_2(CH_2)_aO]_bCH\{CH_2[OCH_2(CH_2)_c]_d X_5\}_2$, $NH(CH_2CH_2NH)_rCH_2CH_2X_5$, $NHCH_2(CH_2)_qX_6$, or $OCH_2(CH_2)_qX_6$; $R^T$ is n-pentyl, sec-pentyl, or iso-pentyl; $X_1$ is $NH_2$, $NHR^{A1}$, $NR^{A1}R^{A2}$, or $NR^{A1}R^{A2}R^{A3}$; $X_2$ is OH, $OR^{B1}$, or $OCH_2(CH_2)_vZ_1$; $X_3$ is $NH_2$, $NHR^{C1}$, $NR^{C1}R^{C2}$, or $NR^{C1}R^{C2}R^{C3}$, or $NHCH_2(CH_2)_vZ_1$; $X_4$ is $NR^{D1}R^{D2}R^{D3}$ or $NHCH_2(CH_2)_vZ_1$; each $X_5$ is, independently, selected from OH, $OR^{E1}$, $NH_2$, $NHR^{E1}$, $NR^{E1}R^{E2}$, $NR^{E1}R^{E2}R^{E3}$, $OCH_2(CH_2)_vZ$, and $NHCH_2(CH_2)_vZ_1$; $X_6$ is selected from $NR^{F1}R^{F2}R^{F3}$ and $Z_1$; a is an integer from 1 to 2; b is an integer from 0 to 3; c is an integer from 1 to 2; d is an integer from 0 to 3; n is an integer from 1 to 5; m is an integer from 1 to 5; p is an integer from 1 to 5; r is an integer from 1 to 5; q is an integer from 1 to 3; v is an integer from 1 to 3; each of $R^{A1}$, $R^{A2}$, $R^{A3}$, $R^{B1}$, $R^{C1}$, $R^{C2}$, $R^{C3}$, $R^{D1}$, $R^{D2}$, $R^{D3}$, $R^{E1}$, $R^{E2}$, $R^{E3}$, $R^{F1}$, $R^{F2}$, and $R^{F3}$ is, independently, selected from $CH_3$, $CH_2CH_3$, $CH_2CH_2CH_3$, and $CH(CH_3)_2$; $Z_1$ is selected from:

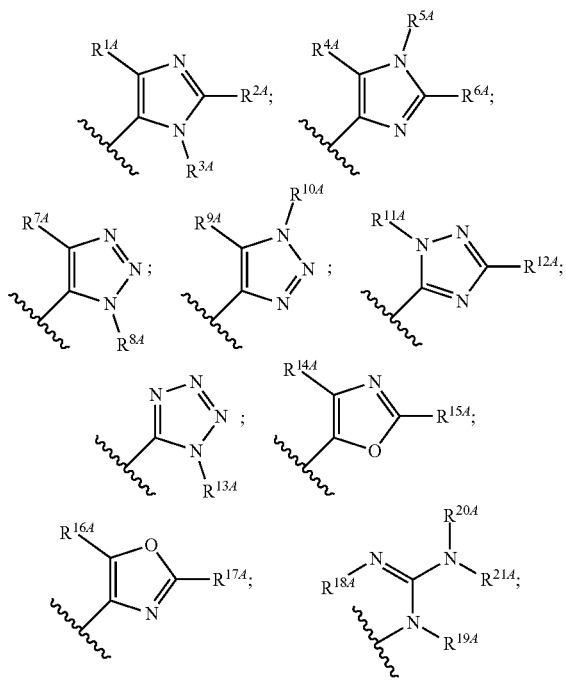

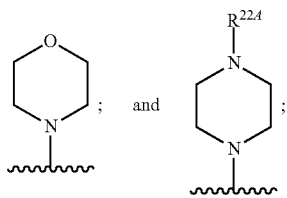

and each of $R^{1A}$, $R^{2A}$, $R^{3A}$, $R^{4A}$, $R^{5A}$, $R^{6A}$, $R^{7A}$, $R^{8A}$, $R^{9A}$, $R^{10A}$, $R^{11A}$, $R^{12A}$, $R^{13A}$, $R^{14A}$, $R^{15A}$, $R^{16A}$, $R^{17A}$, $R^{18A}$, $R^{19A}$, $R^{20A}$, $R^{21A}$, and $R^{22A}$ is, independently, selected from H, $CH_3$, $CH_2CH_3$, $CH_2CH_2CH_3$, and $CH(CH_3)_2$.

In some embodiments of the compounds of formulas (I)-(III), $R^1$ is $O(CH_2CH_2O)_nCH_2CH_2X_1$, $O(CH_2CH_2NH)_n CH_2CH_2X$, $O(CH_2CH_2CH_2O)_nCH_2CH_2X_1$, $NHCH_2CH_2X_2$, $NH(CH_2CH_2O)_mCH_2CH_2X_2$, $NH(CH_2CH_2CH_2O)_mCH_2CH_2X_2$, $NH(CH_2CH_2O)_p CH_2CH_2X_3$, $NH(CH_2CH_2CH_2O)_pCH_2CH_2X_3$, $NHCH_2CH_2X_4$, $NH[CH_2(CH_2)_aO]_bCH\{CH_2[OCH_2 (CH_2)_c]_d X_5\}_2$, $O[CH_2(CH_2)_aO]_bCH\{CH_2[OCH_2(CH_2)_c]_d X_5\}_2$, $NH(CH_2CH_2NH)_rCH_2CH_2X_5$, $NHCH_2(CH_2)_qX_6$, or $OCH_2(CH_2)_qX_6$; $R^T$ is n-pentyl, sec-pentyl, or iso-pentyl; $X_1$ is $NH_2$, $NHR^{A1}$, $NR^{A1}R^{A2}$, or $NR^{A1}R^{A2}R^{A3}$; $X_2$ is OH or $OR^{B1}$; $X_3$ is $NH_2$, $NHR^{C1}$, $NR^{C1}R^{C2}$, or $NR^{C1}R^{C2}R^{C3}$; $X_4$ is $NR^{D1}R^{D2}R^{D3}$; each $X_5$ is, independently, selected from OH, $OR^{E1}$, $NH_2$, $NHR^{E1}$, $NR^{E1}R^{E2}$, and $NR^{E1}R^{E2}R^{E3}$; $X_6$ is selected from $NR^{F1}R^{F2}R^{F3}$; a is an integer from 1 to 2; b is an integer from 0 to 3; c is an integer from 1 to 2; d is an integer from 0 to 3; n is an integer from 1 to 5; m is an integer from 1 to 5; p is an integer from 1 to 5; r is an integer from 1 to 5; q is an integer from 1 to 3; and each of $R^{A1}$, $R^{A2}$, $R^{A3}$, $R^{B1}$, $R^{C1}$, $R^{C2}$, $R^{C3}$, $R^{D1}$, $R^{D2}$, $R^{D3}$, $R^{E1}$, $R^{E2}$, $R^{E3}$, $R^{F1}$, $R^{F2}$, and $R^{F3}$ is, independently, selected from $CH_3$, $CH_2CH_3$, $CH_2CH_2CH_3$, and $CH(CH_3)_2$. In some embodiments, one of $X_1$, $X_3$, $X_4$, $X_5$, and $X_6$ is selected from $N(CH_3)_3^+$ and $N(CH_2CH_3)_3^+$.

In some embodiments of the compounds of formulas (I)-(III), $R^1$ is $O(CH_2CH_2O)_nCH_2CH_2X_1$, $O(CH_2CH_2NH)_n CH_2CH_2X_1$, $O(CH_2CH_2CH_2O)_nCH_2CH_2X_1$, $NHCH_2CH_2X_2$, $NH(CH_2CH_2O)_mCH_2CH_2X_2$, $NH(CH_2CH_2CH_2O)_mCH_2CH_2X_2$, $NH(CH_2CH_2O)_p CH_2CH_2X_3$, $NH(CH_2CH_2CH_2O)_pCH_2CH_2X_3$, $NH CH_2CH_2X_4$, $NH[CH_2(CH_2)_aO]_bCH\{CH_2[OCH_2(CH_2)_c]_d X_5\}_2$, $O[CH_2(CH_2)_aO]_bCH\{CH_2[OCH_2(CH_2)_c]_d X_5\}_2$, $NH(CH_2CH_2NH)_rCH_2CH_2X_5$, $NHCH_2(CH_2)_qX_6$, or $OCH_2 (CH_2)_qX_6$; $R^T$ is n-pentyl, sec-pentyl, or iso-pentyl; $X_1$ is $NHCH_2(CH_2)_vZ_1$; $X_2$ is $OCH_2(CH_2)_vZ_1$; $X_3$ is $NHCH_2 (CH_2)_vZ_1$; $X_4$ is $NHCH_2(CH_2)_vZ_1$; each $X_5$ is, independently, selected from $OCH_2(CH_2)_vZ_1$ and $NHCH_2(CH_2)_vZ_1$; $X_6$ is $Z_1$; a is an integer from 1 to 2; b is an integer from 0 to 3; c is an integer from 1 to 2; d is an integer from 0 to 3; n is an integer from 1 to 5; m is an integer from 1 to 5; p is an integer from 1 to 5; r is an integer from 1 to 5; q is an integer from 1 to 3; v is an integer from 1 to 3; $Z_1$ is selected from:

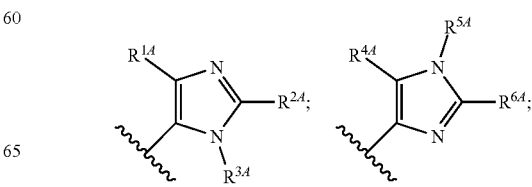

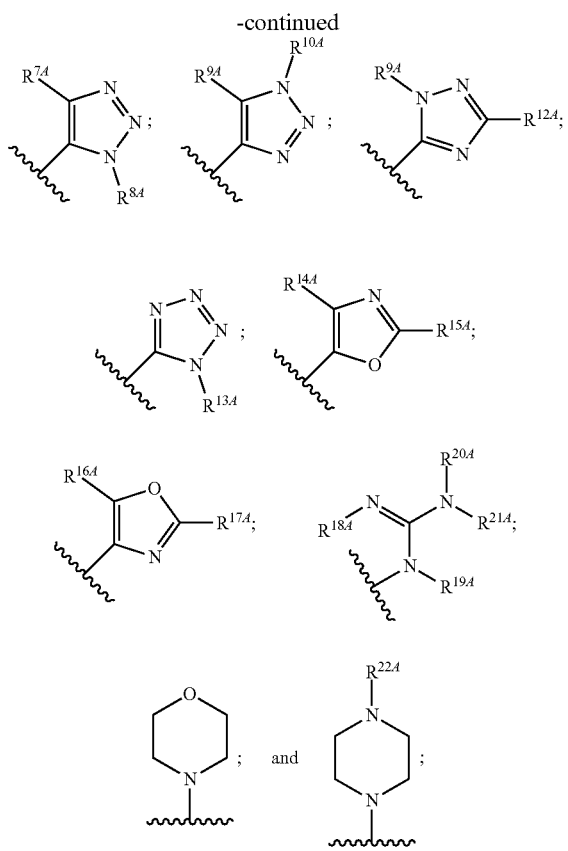

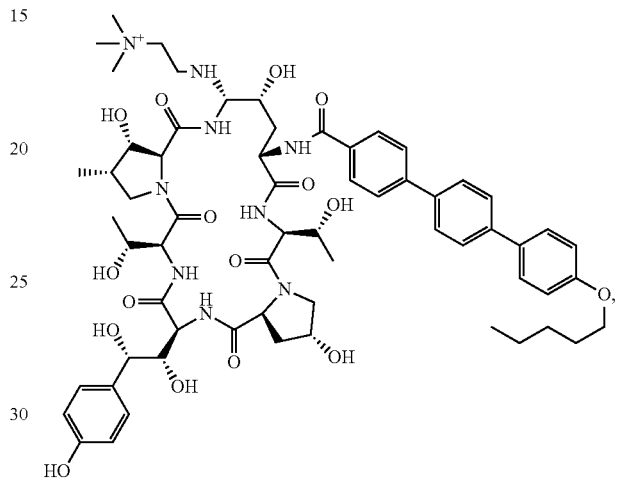

and each of $R^{1A}$, $R^{2A}$, $R^{3A}$, $R^{4A}$, $R^{5A}$, $R^{6A}$, $R^{7A}$, $R^{8A}$, $R^{9A}$, $R^{10A}$, $R^{11A}$, $R^{12A}$, $R^{13A}$, $R^{14A}$, $R^{15A}$, $R^{16A}$, $R^{17A}$, $R^{18A}$, $R^{19A}$, $R^{20A}$, $R^{21A}$, and $R^{22A}$ is, independently, selected from H, $CH_3$, $CH_2CH_3$, $CH_2CH_2CH_3$, and $CH(CH_3)_2$.

In some embodiments of any of the above methods, the compound is a salt of Compound 1:

or a neutral form thereof. In particular embodiments, the methods described herein include administering to the subject doses of about 150 mg to about 800 mg of a salt of Compound 1, or a neutral form thereof, one to three times per week to the subject for a period of 2 to 8 weeks.

In particular embodiments of any of the above methods, the compound is a salt of Compound 2, (Compound 2)

or a neutral form thereof.

In certain embodiments of any of the above methods, the compound is Compound 3, (Compound 1)

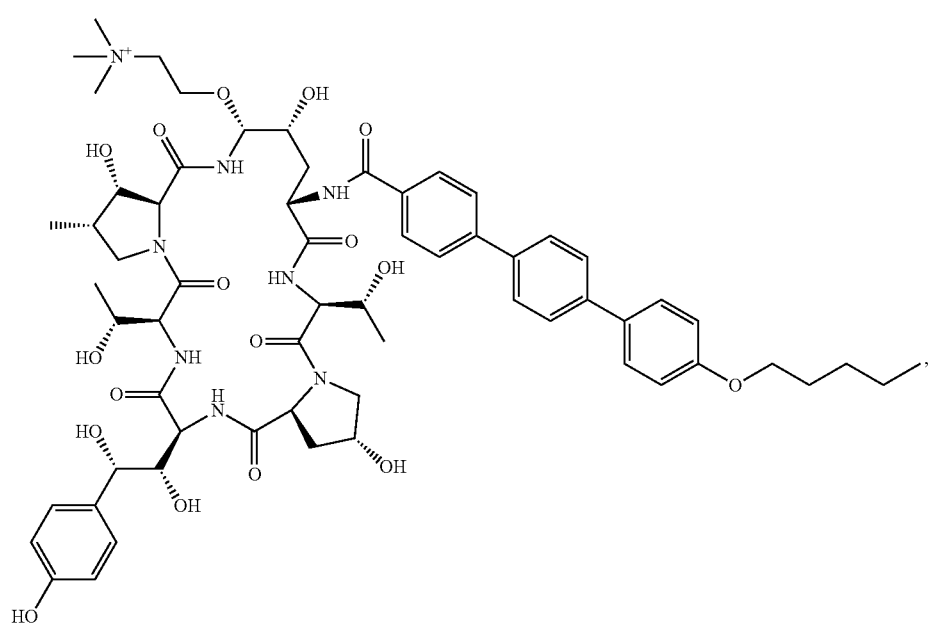

(Compound 3)

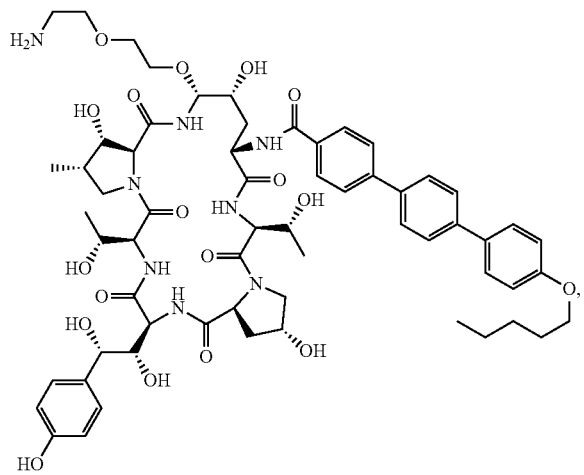

or a pharmaceutically acceptable salt thereof.

In some embodiments of any of the above methods, the compound is selected from Compound 4, Compound 5, Compound 6, Compound 7, Compound 8, Compound 9, Compound 10, Compound 11, Compound 12, Compound 13, Compound 14, Compound 15, Compound 16, Compound 17, Compound 18, Compound 19, and pharmaceutically acceptable salts thereof. Structures of these compounds are depicted in FIG. 3.

In some embodiments, a pharmaceutically acceptable salt of a compound of any of formulas (I)-(III) is used in any of the above methods.

In some embodiments of the second and third aspects of the disclosure, the method includes weekly dosing of Compound 1 in salt or neutral form, and includes (a) intravenously administering a first dose of about 400 mg of Compound 1 in salt or neutral form, (b) intravenously administering a subsequent dose of about 200 mg of Compound 1 in salt or neutral form, and (c) optionally repeating step (b) for one to ten weeks.

In some embodiments of the second and third aspects of the disclosure, the method consists of (a) intravenously administering a first dose of about 400 mg of Compound 1 in salt or neutral form, (b) intravenously administering a second dose of 200 mg of Compound 1 in salt or neutral form, and (c) optionally intravenously administering a third dose of about 200 mg of Compound 1 in salt or neutral form, wherein the first dose is administered on day 1, the second dose is administered on day 8, and the third dose, if administered, is administered on day 15.

In some embodiments of the second and third aspects of the disclosure, the method includes weekly dosing of Compound 1 in salt or neutral form, and includes (a) intravenously administering a dose of about 400 mg of Compound 1 in salt or neutral form, (b) intravenously administering a subsequent dose of about 400 mg of Compound 1 in salt or neutral form, and (c) optionally repeating step (b) for one to ten weeks.

In some embodiments of the second and third aspects of the disclosure, the method consists of (a) intravenously administering a first dose of about 400 mg of Compound 1 in salt or neutral form, (b) intravenously administering a second dose of about 400 mg of Compound 1 in salt or neutral form, and (c) optionally intravenously administering a third dose of about 400 mg of Compound 1 in salt or neutral form, wherein the first dose is administered on day 1, the second dose is administered on day 8, and the third dose, if administered, is administered on day 15.

In some embodiments, the third dose of about 200 mg of Compound 1 in salt or neutral form is administered if on day 15 mycological eradication and/or clinical cure has not been achieved in the subject. In other embodiments, the third dose including 200 mg of Compound 1 in salt or neutral form is not administered if mycological eradication has been achieved in the subject.

In some embodiments, the third dose of about 400 mg of Compound 1 in salt or neutral form is administered if on day 15 mycological eradication and/or clinical cure has not been achieved in the subject. In other embodiments, the third dose including 400 mg of Compound 1 in salt or neutral form is not administered if mycological eradication has been achieved in the subject.

In some embodiments, mycological eradication is determined by two negative blood cultures drawn at ≥12 hours apart without intervening positive blood cultures.

In some embodiments, the third dose of about 200 mg of Compound 1 in salt or neutral form is administered if on day 15 the subject displays symptoms of a fungal infection. In some embodiments, the third dose of about 400 mg of Compound 1 in salt or neutral form is administered if on day 15 the subject displays symptoms of a fungal infection. In some embodiments, symptoms of the fungal infection includes fever, cough, shortness of breath, weight loss, and/or night sweats.

In a fourth aspect, the disclosure features a method of administering Compound 1 to a subject (e.g., a human), wherein the method consisting of (a) intravenously administering a first dose including 400 mg of Compound 1 in salt or neutral form, (b) intravenously administering a second dose including 200 mg of Compound 1 in salt or neutral form, and (c) optionally intravenously administering a third dose including 200 mg of Compound 1 in salt or neutral form, wherein the first dose is administered on day 1, the second dose is administered on day 8, and the third dose, if administered, is administered on day 15.

In a fifth aspect, the disclosure features a method of administering Compound 1 to a subject (e.g., a human), wherein the method consisting of (a) intravenously administering a first dose including 400 mg of Compound 1 in salt or neutral form, (b) intravenously administering a second dose including 400 mg of Compound 1 in salt or neutral form, and (c) optionally intravenously administering a third dose including 400 mg of Compound 1 in salt or neutral form, wherein the first dose is administered on day 1, the second dose is administered on day 8, and the third dose, if administered, is administered on day 15.

In some embodiments, Compound 1 is administered over a time period of 30 to 180 minutes (e.g., over 30±5 minutes, 60±5 minutes, 90±5 minutes, 120±5 minutes, 150±5 minutes, or 180±5 minutes). In some embodiments, Compound 1 is administered as an aqueous pharmaceutical composition. In some embodiments, the pharmaceutical composition has a pH of from 4.0 to 8. In some embodiments, Compound 1 salt is Compound 1 acetate.

As used herein, the amount in each dose refers to the amount of Compound 1 (structure shown above) that does not include the negative counterion (e.g., an acetate) if Compound 1 is in its salt form. For example, a dose of about 400 mg or 200 mg of Compound 1 in salt or neutral form refers to 400 mg or 200 mg of Compound 1, not including the acetate ion if Compound 1 is in an acetate salt form.

In some embodiments of the methods described herein, Compound 1 in salt or neutral form is administered for a predetermined period of 2-12 doses (e.g., 2-3 doses). In some embodiments, Compound 1 in salt or neutral form is administered until mycological eradication as determined by a standard test known in the art. In some embodiments, mycological eradication is defined as two negative blood cultures drawn at ≥12 hours apart without intervening positive blood cultures and no change of antifungal therapy for the fungal infection (e.g., a *Pneumocystis* infection). In some embodiments, Compound 1 in salt or neutral form is administered until the subject is free of symptoms of the fungal infection (e.g., a *Pneumocystis* infection), such as fever, cough, shortness of breath, weight loss, and night sweats, as determined by a physician.

In some embodiments of methods of reducing the risk of a *Pneumocystis* infection in a subject, more than 3 doses (e.g., 4, 5, 6, 7, 8, 9, or 10 doses) of Compound 1 in salt or neutral form is administered to the subject. In some embodiments, the first dose includes about 400 mg of Compound 1 in salt or neutral form, and the remaining doses each includes about 200 mg of Compound 1 in salt or neutral form. In some embodiments, all doses each includes about 400 mg of Compound 1 in salt or neutral form.

Definitions

As used herein, the term "*Pneumocystis* infection" refers to a fungal infection caused by a fungus in the genus *Pneumocystis*, e.g., *P. carinii, P. jirovecii, P. murina, P. oryctolagi*, and *P. wakefieldiae*.

As used herein, the term "reducing the risk of a *Pneumocystis* infection" refers to reducing the likelihood of a subject (e.g., a human) getting a *Pneumocystis* infection. The subject receiving prophylactic therapy can be a subject in need of such treatment, such as an immunocompromised subject.

As used herein, the term "inhibiting the reproduction or growth of a *Pneumocystis* spp." refers to reducing or preventing the reproduction of a *Pneumocystis* spp., reducing or preventing the formation or growth of the cyst form of a *Pneumocystis* spp. and/or and reducing or preventing the formation of the trophic form of a *Pneumocystis* spp. In some embodiments, the term refers to reducing the formation of the cyst form of a *Pneumocystis* spp. or preventing the formation of the cyst form of a *Pneumocystis* spp. In some embodiments, the term refers to reducing the growth of the cyst form of a *Pneumocystis* spp. or preventing the growth of the cyst form of a *Pneumocystis* spp. In some embodiments, the term refers to reducing the formation of the trophic form of a *Pneumocystis* spp. or preventing the formation of the trophic form of a *Pneumocystis* spp. In some embodiments, the term refers to reducing the growth of the trophic form of a *Pneumocystis* spp. or preventing the growth of the trophic form of a *Pneumocystis* spp. As currently understood, and without being bound by theory, *Pneumocystis* spp. exist within a host in two forms: the trophic and the cyst. The trophic forms of *Pneumocystis* spp. may reproduce asexually via binary fission while cysts are able to reproduce sexually after trophozoites conjugate. The cysts develop in three stages with increasing amounts of intracystic nuclei in each stage. The early cyst stage contains two intracystic nuclei while the intermediate stage has four and the late precysts stage holds eight. The mature cysts then release the trophic form of *Pneumocystis* spp. as they burst. The methods described herein can be useful for inhibiting the formation or growth of the cyst form of *Pneumocystis* spp., and inhibiting the production of the trophic form of a *Pneumocystis* spp.

As used herein, the term "cyst burden" refers to the amount (i.e., number) of cysts present in vivo as measured in tissues of an infected subject, or in vitro as measured in a sample (i.e., a tissue sample) isolated from an infected subject. A cyst refers to a group of encased spores that form the trophic form of a *Pneumocystis* spp. after release from the cyst.

As used herein, the term "*Pneumocystis* pneumonia" refers to an infection caused by *Pneumocystis* spp. (e.g., in humans *Pneumocystis jirovecii*). Depending upon the mammal infected, *Pneumocystis* pneumonia may also be referred to as *Pneumocystis jirovecii* pneumonia, *Pneumocystis carini* pneumonia, or PCP.

As used herein, the term "immunocompromised" refers to a subject (e.g., a human) having a weakened immune system. The subject's immune system can be weakened or compromised by a disease (e.g., an HIV infection, an autoimmune disease, cancer), a medical procedure (e.g., an organ transplant (e.g., a solid organ transplant) or a bone marrow transplant), a drug (e.g., an immunosuppressant), and/or a pathogen (e.g., bacteria, fungus, virus). The immune system of the host may also have a congenital defect that renders the host more susceptible to infection.

As used herein, the term "immunosuppression therapy" refers to a therapy that uses one or more immunosuppressants to reduce the activation and/or efficacy of the immune system of a subject (e.g., a human). In some embodiments, an immunosuppression therapy is used to prevent the body from rejecting a transplant (e.g., an organ transplant (e.g., a solid organ transplant) or a bone marrow transplant), to treat graft-versus-host disease after a bone marrow transplant, and/or to treat autoimmune diseases (e.g., systemic lupus erythematosus, rheumatoid arthritis, Crohn's disease, multiple sclerosis, myasthenia gravis, Sarcoidosis, Behcet's disease). Examples of immunosuppressants include, but are not limited to, calcineurin inhibitors, mTOR inhibitors, and tyrosine kinase inhibitors (e.g., cyclosporine A, cyclosporine G, voclosporin, tacrolimus, pimecrolimus, sirolimus, temsirolimus, deforolimus, everolimus, zotarolimus, biolimus, imatinib, dasatinib, nilotinib, erlotinib, sunitinib, gefitinib, bosutinib, neratinib, axitinib, crizotinib, lapatinib, toceranib and vatalanib).

As used herein, the term "anti-TNF therapy" refers to a therapy that uses small molecule and/or protein drugs to inhibit or prevent tumor necrosis factor (TNF) receptor binding and/or activation by a TNF. TNF signaling is involved in the autoimmune and immune-mediated disorders (e.g., systemic lupus erythematosus, rheumatoid arthritis, Crohn's disease, multiple sclerosis, myasthenia gravis, Sarcoidosis, Behcet's disease). Examples of small molecule and/or protein drugs that target the TNF receptor and/or the TNF include, but are not limited to, infliximab, adalimumab, certolizumab pegol, etanercept, golimumab, xanthine derivatives, and bupropion.

As used herein, the term "corticosteroid therapy" refers to a therapy that uses one or more corticosteroids to treat a variety of diseases and conditions, e.g., immune system-related diseases, inflammatory conditions, and skin diseases. Examples of corticosteroids include, but are not limited to, dexamethasone, prednisone, fludrocortisones, and hydrocortisone.

As used herein, the term "chemotherapy" refers to a cancer treatment that uses one or more anticancer drugs. In cancer treatment, chemotherapy is sometimes used in combination with other therapies, such as radiation and surgery to treat cancer.

As used herein, the term "second antifungal agent" refers to an agent that is used in combination with a compound of any of formulas (I)-(III) (e.g., a salt form of Compound 1) to treat a fungal infection (e.g., a *Pneumocystis* infection). Examples of second antifungal agents include, but are not limited to, any of the antifungal agents described herein.

As used herein, the term "a neutral form" includes zwitterionic forms of compounds bearing a tertiary ammonium ion positive charge (e.g., Compound 1 or Compound 2) in which the compound has no net positive or negative charge. The zwitterion can be present in a higher proportion in basic medium (e.g., pH 9).

As used herein, the terms "intravenous administration" or "intravenously administering" refer to intravenous bolus injection or infusion of a drug to a subject (e.g., a human).

As used herein, the term "about" refers to a range of values that is ±10% of specific value. For example, "about 150 mg" includes ±10% of 150 mg, or from 135 mg to 165 mg. Such a range performs the desired function or achieves the desired result. For example, "about" may refer to an amount that is within less than 10% of, within less than 5% of, within less than 1% of, within less than 0.1% of, and within less than 0.01% of the stated amount.

By "dose" is meant the amount of Compound 1 administered to the subject (e.g., a human).

By "clinical cure" is meant complete resolution of most or all of the clinical signs and symptoms of candidemia which were present at baseline and no new signs/symptoms or complications attributable to candidemia.

DESCRIPTION OF THE DRAWINGS

FIG. 4 shows PK of Compound 1 over doses 1 mg/kg, 4 mg/kg, and 16 mg/kg.

FIG. 5 shows net change in fungal density ($\log_{10}$ CFU) versus different total doses of Compound 1 at different fractionation schedules.

FIG. 6 shows change in fungal density ($\log_{10}$ CFU) reduction from baseline caused by 2 mg/kg total dose of Compound 1 at different fractionation schedules.

FIG. 7 shows simulated free-drug concentration time profiles relative to the MIC for the fractionated Compound 1 2 mg/kg regimen.

DETAILED DESCRIPTION

Figures 1A, 1B:
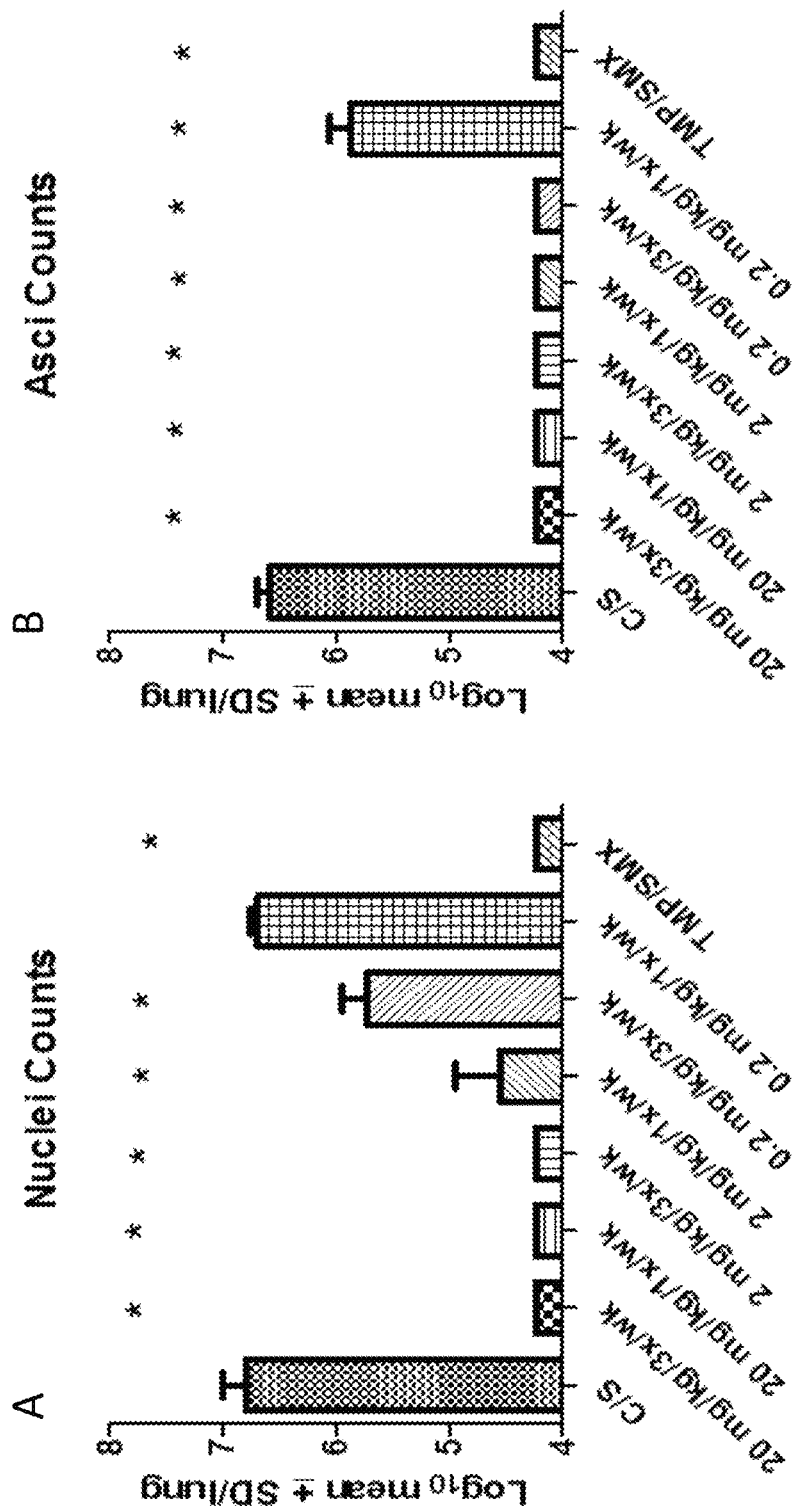
FIG. 1A shows the preventative effects of Compound 1 on lung burdens (shown as nuclei counts) in mice infected with *Pneumocystis* murina.
FIG. 1B shows the preventative effects of Compound 1 on lung burdens (shown as asci counts) in mice infected with *Pneumocystis* murina.

Provided are methods for treating or reducing the risk of a *Pneumocystis* infection (e.g., a *Pneumocystis jirovecii* infection in a human) in a subject (e.g., a human) by administering to the subject a compound of any one of formulas (I)-(III) (e.g., a salt of Compound 1, or a neutral form thereof). In some embodiments, the subject is immunocompromised and, thus, especially vulnerable to *Pneumocystis* infection. The disclosure also features methods of inhibiting the replication of a *Pneumocystis* spp.

I. *Pneumocystis* Infection

A *Pneumocystis* infection refers to an infection caused by a fungus in the genus *Pneumocystis*. Fungi in the genus *Pneumocystis* include *P. carinii*, *P. jirovecii*, *P. murina*, *P. oryctolagi*, and *P. wakefieldiae*. *Pneumocystis jirovecii* pneumonia (also called *Pneumocystis carinii* pneumonia, *Pneumocystis* pneumonia, or PCP) caused by *Pneumocystis jirovecii* remains an important cause of morbidity and mortality in immunocompromised human subjects. PCP is not commonly found in the lungs of healthy subjects, but it can cause lung infections in subjects with weak immune systems. Within the alveolar lumen, *Pneumocystis* spp. appear to have a bi-phasic life cycle consisting of an asexual phase characterized by binary fission of trophic forms and a sexual cycle resulting in formation of cysts. The cysts express 1,3-β-D-glucan synthase and contain 1,3-β-D-glucan. Some signs and symptoms of PCP include, but are not limited to, fever, cough, shortness of breath, weight loss, and night sweats. In certain cases, the fungi can invade other organs, such as the brain, liver, spleen, and kidney. Pneumothorax is often a complication of PCP. Diagnosis of PCP can be confirmed by techniques and methods well-known in the art, e.g., chest x-ray and/or gallium 67 scans. The diagnosis can also be confirmed by histological identification of the causative organism in sputum or bronchio-alveolar lavage. Staining with, e.g., toluidine blue, silver stain, or periodic-acid Schiff stain, or an immunofluorescence assay often shows the characteristic cysts and/or trophic forms.

There is a significant need for prophylaxis against PCP, especially in immunocompromised subjects. However, routine, continuous cultivation of *Pneumocystis* in vitro for testing of susceptibility to antimicrobial agents has not been achieved. Immunosuppressed-rodent models of *Pneumocystis* infection have been highly predictive of the clinical efficacy of standard of care anti-*Pneumocystis* therapies, e.g., trimethoprim-sulfamethoxazole (TMP-SMX) and dapsone. TMP-SMX targets dihydropteroate synthase (DHPS) and dihydrofolate reductase (DHFR). However, up to one-third of subjects with PCP are intolerant of or fail to respond to treatment with TMP-SMX. Toxicity associated with the administration of TMP-SMX include, e.g., fever, rash, headache, nausea, vomiting, neutropenia, pancytopenia, meningitis, nephrotoxicity, anaphylaxis, hepatitis, hyperkalemia, and hypoglycemia. Dapsone is an inhibitor of DHPS. Administration of dapsone also causes adverse reactions, e.g., agranulocytosis, aplastic anemia, rash, nausea, malaise, and a sulfone syndrome (fever, rash, hepatitis, lymphadenopathy, and methemoglobinemia).

Most subjects with PCP have had some identifiable defect in T-cell immunity. PCP has been associated with a broad array of immune deficits. Examples of immune deficits include, but are not limited to, those caused by a human immunodeficiency virus (HIV) infection, a hyper IgM syndrome, cancers, autoimmune diseases, neutropenia, CD4 lymphopenia, hematologic disorders, a congenital immune deficiency, Cushing's syndrome, a nephrotic syndrome, an organ transplant (e.g., a solid organ transplant), a bone marrow transplant, a radiation therapy, one or more immunosuppressants (e.g., corticosteroids), an immunosuppressive therapy, an anti-TNF therapy, a corticosteroid therapy, and/or a chemotherapy. As described in detail further herein, an immunocompromised subject is especially vulnerable to a *Pneumocystis* infection (e.g., a *Pneumocystis jirovecii* infection or PCP).

II. Immunocompromised Subjects

Immunocompromised subjects (e.g., a human) are especially vulnerable to *Pneumocystis* infections. An immunocompromised subject has an immune system that is weakened by a disease or disorder, a medical procedure (e.g., a transplantation procedure or a surgery), a drug (e.g., an immunosuppressive agent), and/or a pathogen (e.g., bacteria, fungus, virus). In some embodiments, a subject's immune system is compromised by the treatment of any of the diseases or disorders described further herein. In some embodiments, a subject (e.g., an immunocompromised subject) is about to have, is currently having, or has had a disease or disorder that weakens the immune system. In some embodiments, a subject (e.g., an immunocompromised subject) is about to undergo or has undergone a transplantation procedure (e.g., an organ transplant (e.g., a solid organ transplant) or a bone marrow transplant) or a radiation therapy. In some embodiments, a subject (e.g., an immunocompromised subject) is about to be administered, is currently administered, or has been administered one or more drugs that weaken the immune system, e.g., an immunosuppressant (e.g., a corticosteroid). In some embodiments, a subject (e.g., an immunocompromised subject) is about to undergo, is currently undergoing, or has undergone an immunosuppressive therapy, an anti-TNF therapy, a corticosteroid therapy, and/or a chemotherapy. In some embodiments, a subject's immune system is compromised by a pathogen (e.g., bacteria, fungus, virus), i.e., either the pathogen is currently present within the subject or had previously infected the subject.

In some embodiments, a subject (e.g., an immunocompromised subject) is HIV positive or has hyper IgM syndrome. In some embodiments, a subject (e.g., an immunocompromised subject) has a CD4$^+$ T-cell count of less than 200 cells/µl of blood. In some embodiments, methods described herein may be used to reduce the risk of or to treat a *Pneumocystis* infection (e.g., a *Pneumocystis jirovecii* infection or PCP) in a subject who is HIV positive or has hyper IgM syndrome. In some embodiments, methods described herein may be used to reduce the risk of or to treat a *Pneumocystis* infection (e.g., a *Pneumocystis jirovecii* infection or PCP) in a subject having a CD4$^+$ T-cell count of less than 200 cells/µl of blood.

Examples of diseases and disorders that weaken a subject's immune system include, but are not limited to, a human immunodeficiency virus (HIV) infection, a hyper IgM syndrome, cancers, autoimmune diseases, neutropenia, CD4 lymphopenia, hematologic disorders, a congenital immune deficiency, Cushing's syndrome, and a nephrotic syndrome. Examples of cancers that weaken a subject's immune system include, but are not limited to, leukemia (e.g., acute lymphoblastic leukemia (ALL), acute myeloid leukemia (AML), chronic myeloid leukemia (CML), small lymphocytic lymphoma (SLL), chronic lymphocytic leukemia (CLL), acute monocytic leukemia (AMOL), and erythroleukemia), Hodgkin's lymphoma, and non-Hodgkin's lymphoma (e.g., lymphoblastic lymphoma, small cell lymphoma (Burkitt's/Non-Burkitt's), and large cell lymphoma). Other cancers that may weaken a subject's immune system include, but are not limited to, bladder cancer, pancreatic cancer, lung cancer, liver cancer, ovarian cancer, colon cancer, stomach cancer, breast cancer, prostate cancer, renal cancer, testicular cancer, thyroid cancer, uterine cancer, rectal cancer, a cancer of the respiratory system, a cancer of the urinary system, oral cavity cancer, skin cancer, larynx cancer, sarcoma, carcinoma, basal cell carcinoma, choriocarcinoma, adenocarcinoma, giant (or oat) cell carcinoma, breast carcinoma, squamous cell carcinoma, multiple myeloma (MM), astrocytoma, oligoastrocytoma, biliary tract cancer, CNS cancer, neuroblastoma, glioblastoma, rhabdomyosarcoma, neuroectodermal cancer, melanoma, inflammatory myofibroblastic tumor and soft tissue tumor. Subjects having a disease or disorder that weaken a subject's immune system can reduce their risk of developing a *Pneumocystis* infection using the methods disclosed herein.

Examples of autoimmune diseases that weaken a subject's immune system include, but are not limited to, alopecia areata, ankylosing spondylitis, antiphospholipid syndrome, Addison's disease, hemolytic anemia, autoimmune hepatitis, hepatitis, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatricial pemphigoid, limited scleroderma (CREST Syndrome), cold agglutinin disease, Crohn's disease, discoid lupus, essential mixed cryoglobulinemia, fibromyalgia-fibromyositis, Graves' disease, Guillain-Barré syndrome, Hashimoto's thyroiditis, hypothyroidism, inflammatory bowel disease, autoimmune lymphoproliferative syndrome (ALPS), idiopathic pulmonary fibrosis, idiopathic thrombocytopenia purpura (ITP), IgA nephropathy, insulin-dependent diabetes, juvenile arthritis, Lichen planus, lupus, Ménière's disease, mixed connective tissue disease, multiple sclerosis, myasthenia gravis, pemphigus vulgaris, pernicious anemia, polyarteritis nodosa, polychondritis, polyglandular syndromes, polymyalgia rheumatica, polymyositis, dermatomyositis, primary agammaglobulinemia, primary biliary cirrhosis, psoriasis, Raynaud's phenomenon, Reiter's syndrome, rheumatic fever, rheumatoid arthritis, sarcoidosis, scleroderma, Sjögren's syndrome, Stiff-man syndrome, systemic lupus erythematosus, Takayasu arteritis, temporal arteritis/giant cell arteritis, ulcerative colitis, uveitis, vasculitis, vitiligo, and Wegener's granulomatosis. Subjects having an autoimmune disease can reduce their risk of developing a *Pneumocystis* infection using the methods disclosed herein.

The methods described herein can be used to reduce the risk of, or treat, a *Pneumocystis* infection (e.g., a *Pneumocystis jirovecii* infection or PCP) in a subject (e.g., a human) having an HIV infection. PCP is the most common opportunistic infection in subjects with HIV. HIV infects the cells of the immune system by attaching and destroying T-cells (e.g., CD4$^+$ T-cells). An HIV-positive subject with low CD4$^+$ T-cell count is especially susceptible to *Pneumocystis* infections (e.g., *Pneumocystis jirovecii* infections). When an HIV-positive subject's T-cell count falls below 200 cells/µl of blood, the subject may be susceptible to other diseases and/or infections, e.g., microbial infections (e.g., *Pneumocystis* infections), and tuberculosis, cancer.

The methods described herein can be used to reduce the risk of, or treat, a *Pneumocystis* infection (e.g., a *Pneumocystis jirovecii* infection or PCP) in a subject (e.g., a human) having a hyper IgM syndrome. Hyper IgM syndrome refers to a family of genetic disorders in which the level of IgM antibodies is relatively high as a result of a defect in a CD4$^+$ T$_h$2-cell protein (e.g., CD40 ligand). The defect in the CD4$^+$ T$_h$2-cell protein leads to the inability of B-cells to produce antibodies other than IgM. Subjects with hyper IgM syndrome often have a low number of neutrophils and platelets.

The methods described herein can be used to reduce the risk of, or treat, a *Pneumocystis* infection (e.g., a *Pneumo-

*cystis jirovecii* infection or PCP) in a subject having neutropenia. Neutropenia refers to a condition characterized by an abnormally low concentration of neutrophils in the blood. Neutrophils make up the majority of circulating while blood cells and serve as the primary defense against microbial infections.

The methods described herein can be used to reduce the risk of, or treat, a *Pneumocystis* infection (e.g., a *Pneumocystis jirovecii* infection or PCP) in a subject (e.g., a human) having a congenital immune deficiency. A congenital immune deficiency refers to a group of immune deficiency disorders present at the time of birth that are caused by genetic defects. Congenital immune deficiencies may occur as a result of defects in B lymphocytes and/or T lymphocytes. Subjects having a congenital immune deficiency are particularly susceptible to infections of the lung, throat, skin, and ear.

The methods described herein can be used to reduce the risk of, or treat, a *Pneumocystis* infection (e.g., a *Pneumocystis jirovecii* infection or PCP) in a subject (e.g., a human) who has undergone or is about to undergo a transplantation procedure (e.g., an organ transplant (e.g., a solid organ transplant) or a bone marrow transplant). In some embodiments, a subject has undergone or is about to undergo a hematopoietic stem cell transplant. In some embodiments, a subject who has undergone or is about to undergo a hematopoietic stem cell transplant has a hematologic disorder (e.g., leukemia). In some embodiments, a subject who has undergone or is about to undergo a transplantation procedure is administered one or more immunosuppressants before, during, and/or after the transplantation procedure to block the adverse effects of organ or tissue rejection by the immune system, or to treat or reduce complications resulting from the transplantation (e.g., graft-versus-host disease (GVHD) and graft rejection).

The methods described herein can be used to reduce the risk of, or treat, a *Pneumocystis* infection in a subject (e.g., a human) who has undergone or is about to undergo a radiation therapy. Certain types of radiation therapy may cause damage to the immune system. For example, radiation to the underarm area, where the lymph nodes are, may cause damage to the lymph nodes and vessels. Radiation directed at pelvic bones may damage the bone marrow within the bones, thus, reducing the production of red and white blood cells.

The methods described herein can be used to reduce the risk of, or treat, a *Pneumocystis* infection in a subject (e.g., a human) who is about to be administered, is currently administered, or has been administered one or more drugs that weaken the immune system, e.g., an immunosuppressant (e.g., a corticosteroid). In some embodiments, methods described herein may be used to reduce the risk of, or treat, a *Pneumocystis* infection in a subject who is about to undergo, is currently undergoing, or has undergone an immunosuppressive therapy, an anti-TNF therapy, a corticosteroid therapy, and/or a chemotherapy. Examples of immunosuppressants used in an immunosuppressive therapy that weaken a subject's immune system include, but are not limited to, calcineurin inhibitors, mTOR inhibitor, and tyrosine kinase inhibitors (e.g., cyclosporine A, cyclosporine G, voclosporin, tacrolimus, pimecrolimus, sirolimus, temsirolimus, deforolimus, everolimus, zotarolimus, biolimus, imatinib, dasatinib, nilotinib, erlotinib, sunitinib, gefitinib, bosutinib, neratinib, axitinib, crizotinib, lapatinib, toceranib and vatalanib). Examples of small molecule and protein drugs used in an anti-TNF therapy to target the TNF receptor and/or the TNF include, but are not limited to, infliximab, adalimumab, certolizumab pegol, etanercept, golimumab, xanthine derivatives, and bupropion. Examples of corticosteroids in a corticosteroid therapy that weaken a subject's immune system include, but are not limited to, dexamethasone, prednisone, fludrocortisones, and hydrocortisone.

III. Compounds

The methods of the disclosure include the use of compounds of formulas (I)-(III) to reduce the risk of, or treat, a *Pneumocystis* infection. The compounds of formulas (I)-(III) are shown below:

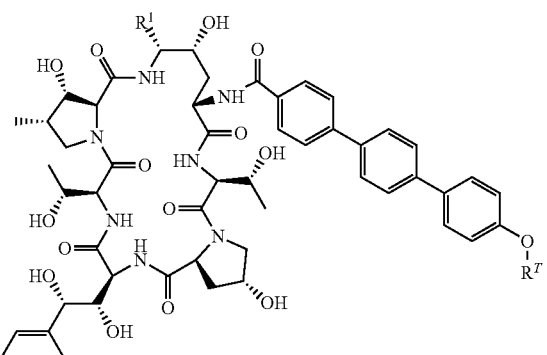

(I)

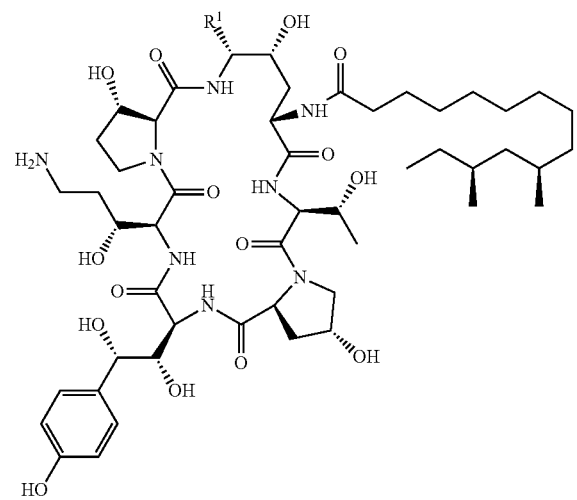

(II)

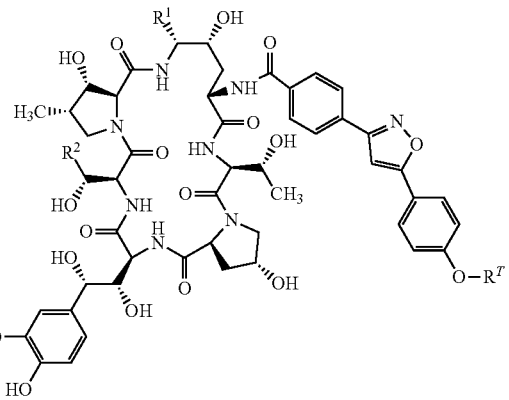

(III)

wherein $R^1$ is $O(CH_2CH_2O)_nCH_2CH_2X_1$, $O(CH_2CH_2NH)_nCH_2CH_2X_1$, $O(CH_2CH_2CH_2O)_nCH_2CH_2X_1$, $NHCH_2CH_2X_2$, $NH(CH_2CH_2O)_mCH_2CH_2X_2$, NH(CH$_2$CH$_2$CH$_2$O)$_m$CH$_2$CH$_2$X$_2$, NH(CH$_2$CH$_2$O)$_p$CH$_2$CH$_2$X$_3$, NH(CH$_2$CH$_2$CH$_2$O)$_p$CH$_2$CH$_2$X$_3$, NHCH$_2$CH$_2$X$_4$, NH[CH$_2$(CH$_2$)$_a$O]$_b$CH{CH$_2$[OCH$_2$(CH$_2$)$_c$]$_d$X$_5$}$_2$, O[CH$_2$(CH$_2$)$_a$O]$_b$CH{CH$_2$[OCH$_2$(CH$_2$)$_c$]$_d$X$_5$}$_2$, NH(CH$_2$CH$_2$NH)$_r$CH$_2$CH$_2$X$_5$, NHCH$_2$(CH$_2$)$_q$X$_6$, or OCH$_2$(CH$_2$)$_q$X$_6$; R$^7$ is n-pentyl, sec-pentyl, or iso-pentyl; X$_1$ is NH$_2$, NHR$^{A1}$, NR$^{A1}$R$^{A2}$, NR$^{A1}$R$^{A2}$R$^{A3}$, or NHCH$_2$(CH$_2$)$_v$Z$_1$; X$_2$ is OH, OR$^{B1}$, or OCH$_2$(CH$_2$)$_v$Z$_1$; X$_3$ is NH$_2$, NHR$^{C1}$, NR$^{C1}$R$^{C2}$, or NR$^{C1}$R$^{C2}$R$^{C3}$, or NHCH$_2$(CH$_2$)$_v$Z$_1$; X$_4$ is NR$^{D1}$R$^{D2}$R$^{D3}$ or NHCH$_2$(CH$_2$)$_v$Z$_1$; each X$_5$ is, independently, selected from OH, OR$^{E1}$, NH$_2$, NHR$^{E1}$, NR$^{E1}$R$^{E2}$, NR$^{E1}$R$^{E2}$R$^{E3}$, OCH$_2$(CH$_2$)$_v$Z, and NHCH$_2$(CH$_2$)$_v$Z$_1$; X$_6$ is selected from NR$^{F1}$R$^{F2}$R$^{F3}$ and Z$_1$; a is an integer from 1 to 2; b is an integer from 0 to 3; c is an integer from 1 to 2; d is an integer from 0 to 3; n is an integer from 1 to 5; m is an integer from 1 to 5; p is an integer from 1 to 5; r is an integer from 1 to 5; q is an integer from 1 to 3; v is an integer from 1 to 3; each of R$^{A1}$, R$^{A2}$, R$^{A3}$, R$^{B1}$, R$^{C1}$, R$^{C2}$, R$^{C3}$, R$^{D1}$, R$^{D2}$, R$^{D3}$, R$^{E1}$, R$^{E2}$, R$^{E3}$, R$^{F1}$, R$^{F2}$, and R$^{F3}$ is, independently, selected from CH$_3$, CH$_2$CH$_3$, CH$_2$CH$_2$CH$_3$, and CH(CH$_3$)$_2$; Z$_1$ is selected from:

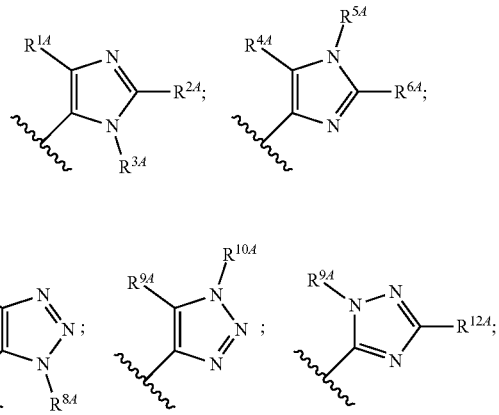

and each of R$^{1A}$, R$^{2A}$, R$^{3A}$, R$^{4A}$, R$^{5A}$, R$^{6A}$, R$^{7A}$, R$^{8A}$, R$^{9A}$, R$^{10A}$, R$^{11A}$, R$^{12A}$, R$^{13A}$, R$^{14A}$, R$^{15A}$, R$^{16A}$, R$^{17A}$, R$^{18A}$, R$^{19A}$, R$^{20A}$, R$^{21A}$, and R$^{22A}$ is, independently, selected from H, CH$_3$, CH$_2$CH$_3$, CH$_2$CH$_2$CH$_3$, and CH(CH$_3$)$_2$.

Figure 3:
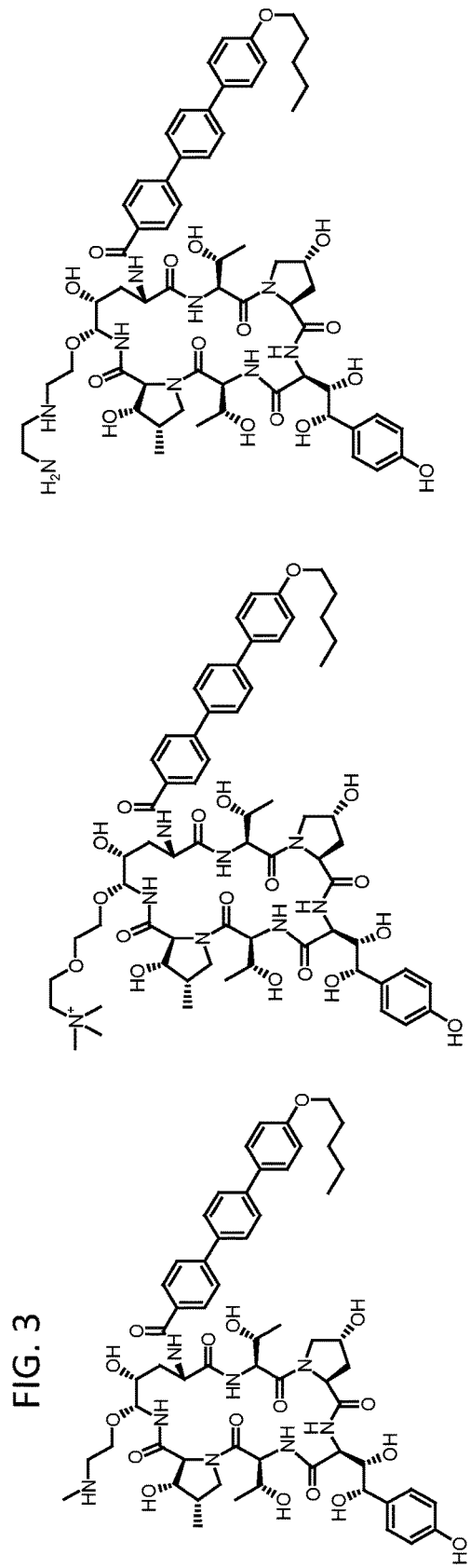
FIG. 3 shows the structures of Compound 4, Compound 5, Compound 6, Compound 7, Compound 8, Compound 9, Compound 10, Compound 11, Compound 12, Compound 13, Compound 14, Compound 15, Compound 16, Compound 17, Compound 18, and Compound 19.
Figure 3:
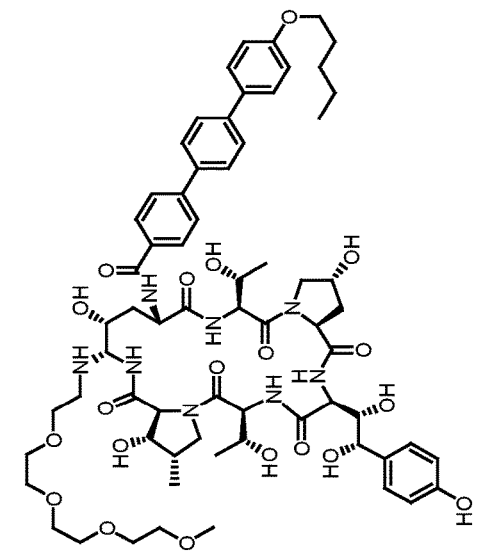
Figure 3:
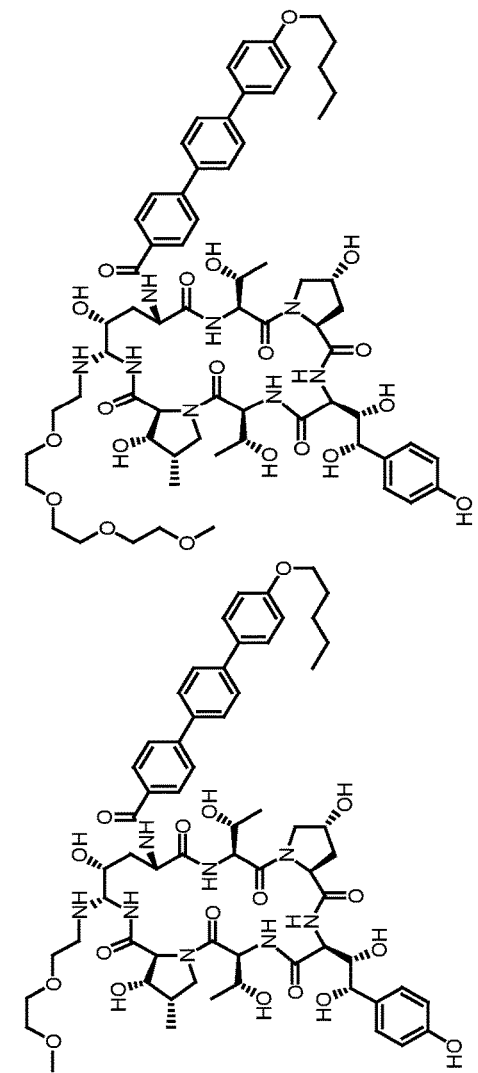
Figure 3:
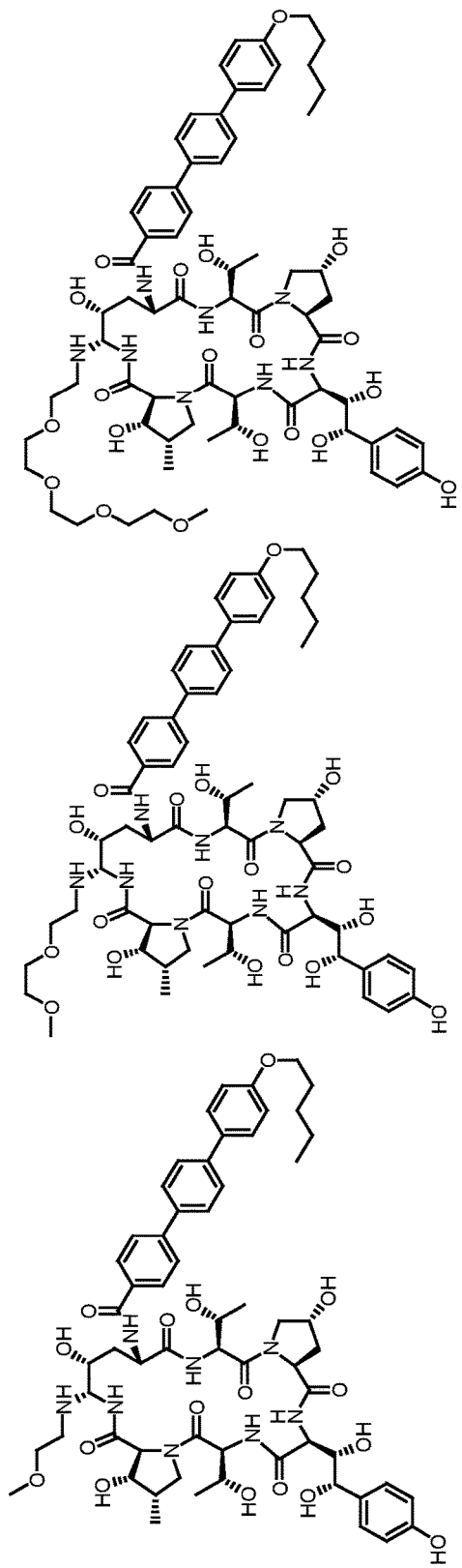
Figure 3:
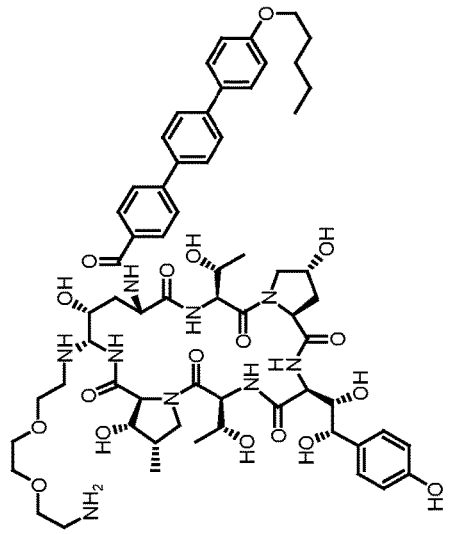
Figure 3:
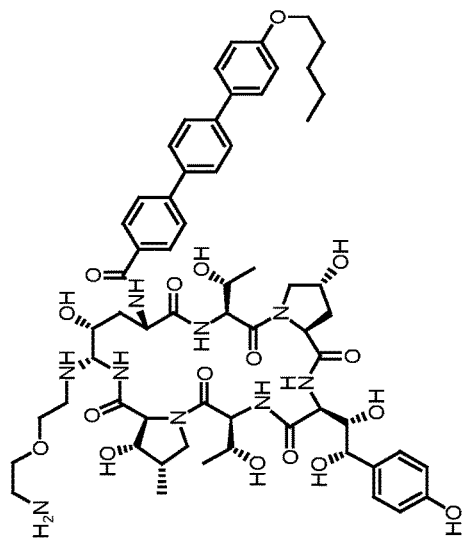
Figure 3:
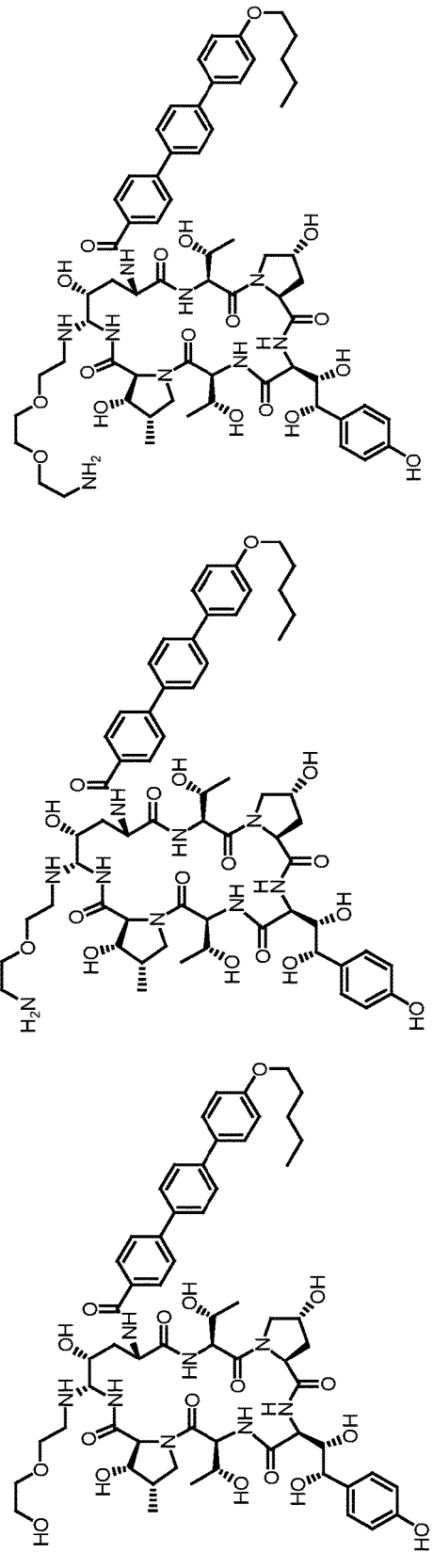
Figure 3:
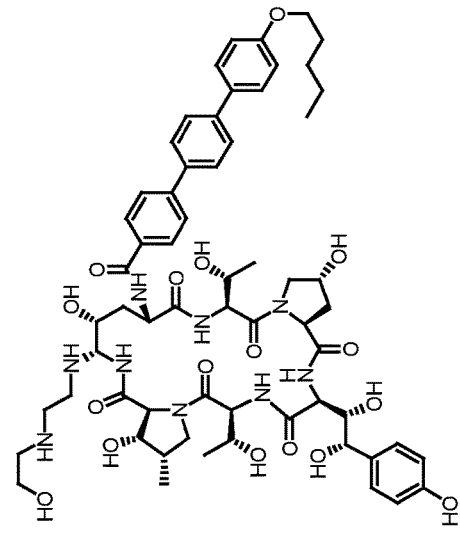
Figure 3:
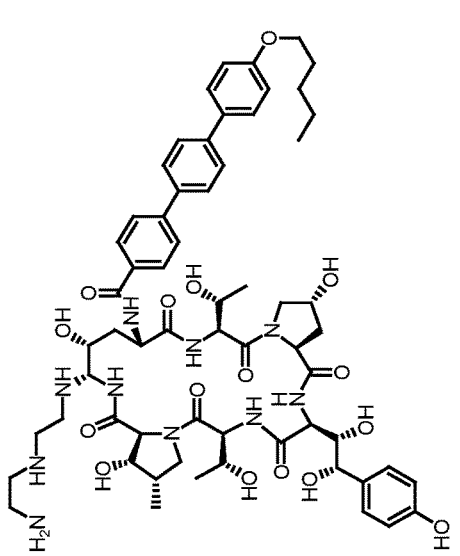
Figure 3:
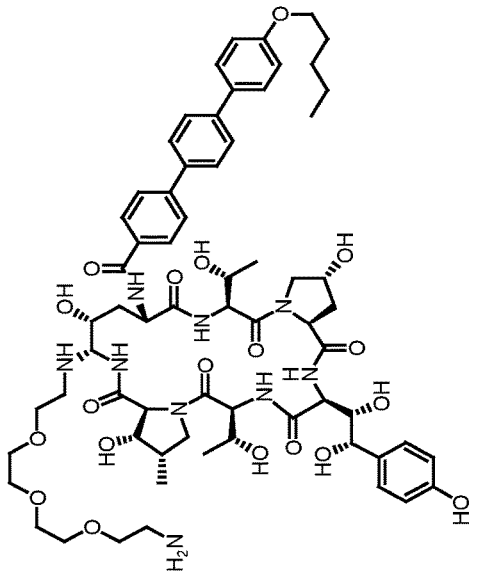
Figure 3:
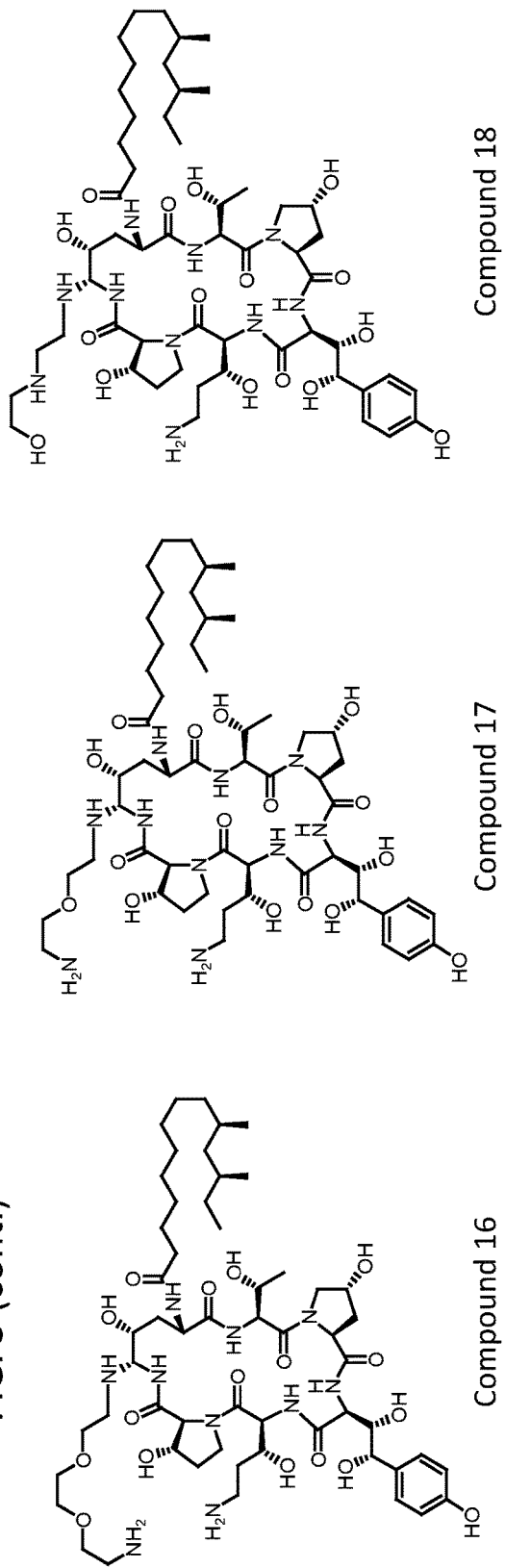

In some embodiments, the compound is selected from Compound 4, Compound 5, Compound 6, Compound 7, Compound 8, Compound 9, Compound 10, Compound 11, Compound 12, Compound 13, Compound 14, Compound 15, Compound 16, Compound 17, Compound 18, Compound 19, and pharmaceutically acceptable salts thereof. The structures of the aforementioned compounds are shown in FIG. 3.

In some embodiments, a salt of Compound 1 (shown below) is used in a method described herein.

(Compound 1)

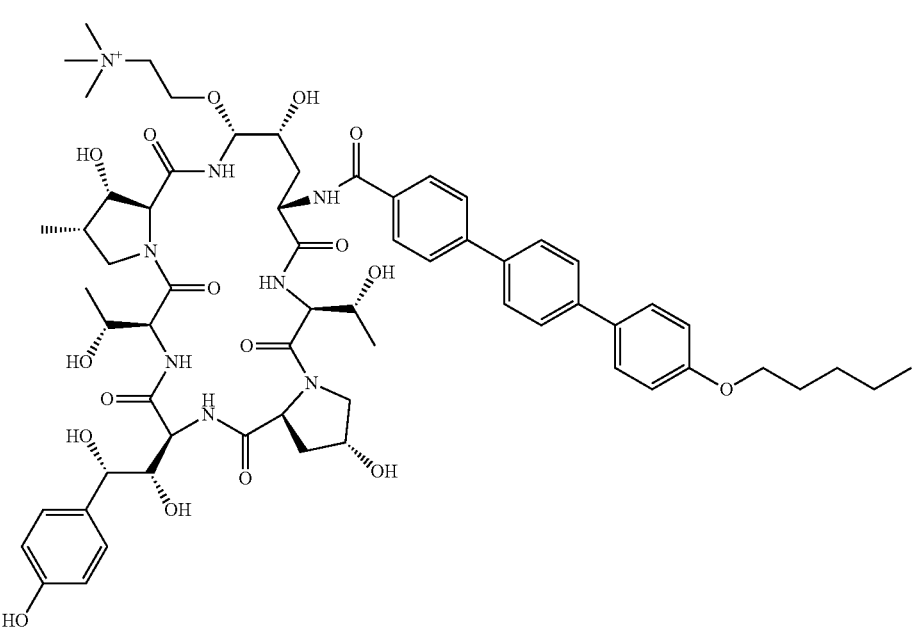

or a neutral form thereof.

In particular embodiments of any of the above methods, the compound is a salt of Compound 2,

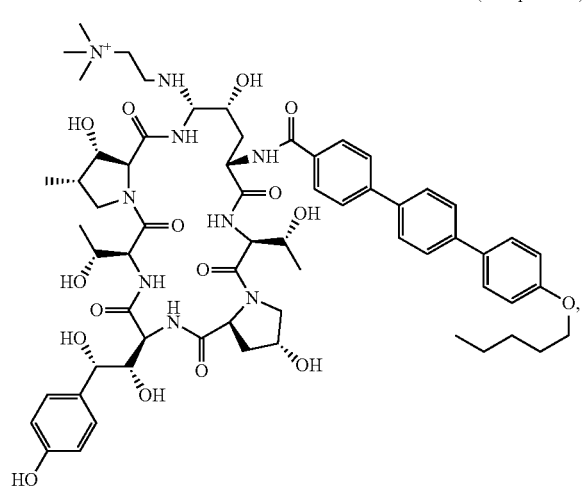

(Compound 2)

or a neutral form thereof.

In certain embodiments of any of the above methods, the compound is Compound 3,

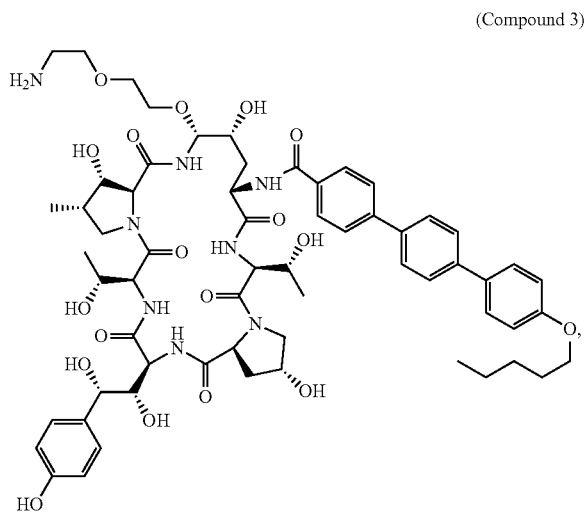 [SMILES: CCCCCOc1ccc(-c2ccc(-c3ccc(C(=O)N[C@H]4C[C@@H](O)[C@@H](OCCOCCN)NC(=O)[C@@H]5[C@@H](O)[C@@H](C)CN5C(=O)[C@H]([C@@H](C)O)NC(=O)[C@H]([C@H](O)[C@@H](O)c5ccc(O)cc5)NC(=O)[C@@H]5C[C@@H](O)CN5C(=O)[C@H]([C@@H](C)O)NC4=O)cc3)cc2)cc1]

(Compound 3)

or a pharmaceutically acceptable salt thereof.

The compounds of formulas (I), (II), and (III) can be synthesized, for example, as described in U.S. Pat. No. 8,722,619, incorporated herein by reference, by coupling functionalized or unfunctionalized echinocandin class compounds with the appropriate acyl, alkyl, hydroxyl, and/or amino groups under standard reaction conditions.

Typically, the semi-synthetic echinocandin class compounds of the disclosure can be made by modifying the naturally occurring echinocandin scaffold. For example, pneumocandin $B_0$ is prepared by fermentation reactions; where fermentation and mixed broths produce a mixture of products which are then separated to produce pneumocandin $B_0$, which is used in the synthesis of caspofungin (see U.S. Pat. No. 6,610,822, which describes extraction of the echinocandin class compounds, such as, pneumocandin $B_0$, WF 11899 and echinocandin B by performing several extraction processes; and see U.S. Pat. No. 6,610,822, which describes methods for purifying the crude extracts).

For semi-synthetic approaches to compounds of the disclosure, the stereochemistry of the compound will be dictated by the starting material. Thus, the stereochemistry of the unnatural echinocandin derivatives will typically have the same stereochemistry as the naturally occurring echinocandin scaffold (representative stereochemistry is depicted in the examples) from which they are derived. Accordingly, any of the compounds shown below anidulafungin, caspofungin, or micafungin can be used as a starting material in the synthesis of the compounds of the disclosure which share the same stereochemical configuration at each of the amino acid residues found in the naturally occurring compound.

Accordingly, the echinocandin class compounds of the disclosure can be derived from the cyclic peptide antifungals which are produced by culturing various microorganisms. For example, amine-terminating compounds can be used to prepare guanidine derivatives. The conversion of amino groups to guanidine groups can be accomplished using standard synthetic protocols. For example, Mosher has described a general method for preparing mono-substituted guanidines by reaction of aminoiminomethanesulfonic acid with amines (Kim, K.; Lin, Y.-T.; Mosher, H. S. *Tetrahedron Lett.* 29: 3183, 1988). A more convenient method for guanylation of primary and secondary amines was developed by Bernatowicz employing 1H-pyrazole-1-carboxamidine hydrochloride; 1-H-pyrazole-1-(N,N'-bis(tert-butoxycarbonyl)carboxamidine; or 1-H-pyrazole-1-(N,N'-bis(benzyloxycarbonyl)carboxamidine. These reagents react with amines to give mono-substituted guanidines (see Bernatowicz et al., *J. Org. Chem.* 57: 2497, 1992; and Bernatowicz et al., *Tetrahedron Lett.* 34: 3389, 1993). In addition, Thioureas and S-alkyl-isothioureas have been shown to be useful intermediates in the syntheses of substituted guanidines (Poss et al., *Tetrahedron Lett.* 33: 5933 1992). The compounds that include a heterocyclic ring can be synthesized, for example, by coupling a hydroxyalkyl or aminoalkyl substituted heterocycle with a parent echinocandin compound using those coupling methods described in U.S. Pat. No. 8,722,619.

IV. Pharmaceutical Compositions and Preparations

A compound of any of formulas (I)-(III) (e.g., a salt of Compound 1, or a neutral form thereof) may be prepared in a pharmaceutical composition. In some embodiments, the pharmaceutical composition includes a compound of any of formulas (I)-(III) (e.g., a salt of Compound 1, or a neutral form thereof) and pharmaceutically acceptable carriers and excipients. Depending on the mode of administration and the dosage, a compound of any of formulas (I)-(III) (e.g., a salt of Compound 1, or a neutral form thereof) used in the methods described herein will be formulated into suitable pharmaceutical compositions to permit facile delivery. A compound of any of formulas (I)-(III) (e.g., a salt of Compound 1, or a neutral form thereof) may be formulated in a variety of ways that are known in the art. For use as treatment of human and animal subjects, a compound of any of formulas (I)-(III) (e.g., a salt of Compound 1, or a neutral form thereof) can be formulated as pharmaceutical or veterinary compositions. Depending on the subject to be treated (e.g., a human), the mode of administration, and the type of treatment desired, e.g., prevention, prophylaxis, or therapeutic therapy, a compound of any of formulas (I)-(III) (e.g., a salt of Compound 1, or a neutral form thereof) is formulated in ways consonant with these parameters. A summary of such techniques is found in *Remington: The Science and Practice of Pharmacy, 22nd Edition*, Lippincott Williams & Wilkins, (2012); and *Encyclopedia of Pharmaceutical Technology*, eds. J. Swarbrick and J. C. Boylan, 2006, Marcel Dekker, New York, each of which is incorporated herein by reference.

Acceptable carriers and excipients in the pharmaceutical compositions are nontoxic to recipients at the dosages and concentrations employed. Acceptable carriers and excipients may include buffers such as phosphate, citrate, HEPES, and TAE, antioxidants such as ascorbic acid and methionine, preservatives such as hexamethonium chloride, octadecyldimethylbenzyl ammonium chloride, resorcinol, and benzalkonium chloride, proteins such as human serum albumin, gelatin, dextran, and immunoglobulins, hydrophilic polymers such as polyvinylpyrrolidone, amino acids such as glycine, glutamine, histidine, and lysine, and carbohydrates such as glucose, mannose, sucrose, and sorbitol.

The pharmaceutical compositions can be prepared in a variety of dosage forms, e.g., intravenous dosage forms, subcutaneous dosage forms, and oral dosage forms (e.g., ingestible solutions, drug release capsules). A compound of any of formulas (I)-(III) (e.g., a salt of Compound 1, or a neutral form thereof) or a pharmaceutical composition of a compound of any of formulas (I)-(III) (e.g., a salt of Compound 1, or a neutral form thereof) may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, preparations suitable for iontophoretic delivery, or aerosols. The compositions may be formulated according to conventional pharmaceutical practice.

The pharmaceutical compositions can be administered parenterally in the form of an injectable formulation. Pharmaceutical compositions for injection can be formulated using a sterile solution or any pharmaceutically acceptable liquid as a vehicle. Pharmaceutically acceptable vehicles include, but are not limited to, sterile water, physiological saline, and cell culture media (e.g., Dulbecco's Modified Eagle Medium (DMEM), α-Modified Eagles Medium (α-MEM), F-12 medium). Formulation methods are known in the art, see e.g., Gibson (ed.) *Pharmaceutical Preformulation and Formulation* ($2^{nd}$ ed.) Taylor & Francis Group, CRC Press (2009).

The pharmaceutical compositions can be prepared in the form of an oral formulation. Formulations for oral use include tablets containing the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like. Formulations for oral use may also be provided as chewable tablets, or as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

The pharmaceutical composition may be formed in a unit dose form as needed. The amount of active component, e.g., a compound of any of formulas (I)-(III) (e.g., a salt of Compound 1, or a neutral form thereof) included in the pharmaceutical compositions are such that a suitable dose within the designated range is provided (e.g., a dose within the range of 0.01-100 mg/kg of body weight).

V. Routes, Dosage, and Administration

A compound of any of formulas (I)-(III) or a pharmaceutical composition including a compound of any of formulas (I)-(III) may be formulated for, e.g., intraoral administration, intravenous administration, intramuscular administration, intradermal administration, intraarterial administration, subcutaneous administration, oral administration, or administration by inhalation. In some embodiments, Compounds of formulas (I)-(III) or pharmaceutical compositions including a compound of any of formulas (I)-(III) may be formulated for intravenous administration. In some embodiments, Compounds of formulas (I)-(III) or pharmaceutical compositions including a compound of any of formulas (I)-(III) may be formulated for administration by inhalation. In some embodiments, Compounds of formulas (I)-(III) or pharmaceutical compositions including a compound of any of formulas (I)-(III) may be formulated for oral administration. For injectable formulations, various effective pharmaceutical carriers are known in the art. See, e.g., Remington: The Science and Practice of Pharmacy, $22^{nd}$ ed., (2012) and ASHP Handbook on Injectable Drugs, $18^{th}$ ed., (2014).

The dosage of a compound of any of formulas (I)-(III) or a pharmaceutical composition including a compound of any of formulas (I)-(III) depends on factors including the route of administration, the disease to be treated, and physical characteristics, e.g., age, weight, general health, of the subject (e.g., a human). The dosage may be adapted by the physician in accordance with conventional factors such as the extent of the disease and different parameters of the subject. Typically, the amount of a compound of any of formulas (I)-(Ill) or a pharmaceutical composition including a compound of any of formulas (I)-(III) contained within one or more doses may be an amount that effectively reduces the risk of or treats a *Pneumocystis* infection in a subject without inducing significant toxicity.

In any of the methods described herein, the compound of formula (I)-(III), or a pharmaceutically acceptable salt thereof, can be administered in doses of about 50 mg to about 1 g (e.g., about 50 mg to about 1 g, about 75 mg to about 950 mg, about 100 mg to about 900 mg, about 125 mg to about 850 mg, about 150 mg to about 800 mg, about 175 mg to about 750 mg, about 200 mg to about 700 mg, about 200 mg to about 400 mg, about 250 mg to about 650 mg, about 300 mg to about 600 mg, about 350 mg to about 550 mg, about 400 mg to about 500 mg, about 425 mg to about 475 mg, e.g., about 150 mg to about 800 mg) of a compound of any of formulas (I)-(III) (e.g., a salt of Compound 1, or a neutral form thereof) are administered to a subject one to three times per week for 2 to 8 weeks (e.g., 2 to 8 weeks, 2 to 7 weeks, 2 to 6 weeks, 2 to 5 weeks, 2 to 4 weeks, or 2 to 3 weeks). In some embodiments of the methods described herein, doses of about 50 mg to about 1 g (e.g., about 50 mg to about 1 g, about 75 mg to about 950 mg, about 100 mg to about 900 mg, about 125 mg to about 850 mg, about 150 mg to about 800 mg, about 175 mg to about 750 mg, about 200 mg to about 700 mg, about 250 mg to about 650 mg, about 300 mg to about 600 mg, about 350 mg to about 550 mg, about 400 mg to about 500 mg, about 425 mg to about 475 mg, e.g., about 150 mg to about 800 mg) of a compound of any of formulas (I)-(III) (e.g., a salt of Compound 1, or a neutral form thereof) are administered to a subject one to three times per week for 2 to 8 weeks.

In some embodiments of the methods described herein, doses of about 150 mg to about 800 mg of a compound of any of formulas (I)-(III) (e.g., a salt of Compound 1, or a neutral form thereof) are administered to a subject one to three times per week for 2 to 8 weeks (e.g., 2 to 8 weeks, 2 to 7 weeks, 2 to 6 weeks, 2 to 5 weeks, 2 to 4 weeks, or 2 to 3 weeks).

In some embodiments of the methods described herein, doses of about 150 mg to about 800 mg of a salt of Compound 1, or a neutral form thereof, are administered to a subject one to three times per week for 2 to 8 weeks.

In some methods, a salt of Compound 1, or a neutral form thereof is intravenously administered to a subject (e.g., a human) in two or more weekly doses (e.g., 2, 3, 4, 5, 6, 7, 8, 9, 10, 11, or 12 doses), wherein the first dose contains about 400 mg of a salt of Compound 1, or a neutral form thereof and each of the subsequent doses contains about 200 mg of a salt of Compound 1, or a neutral form thereof. In some embodiments, the first dose includes about 400 mg of Compound 1, or a salt or neutral form thereof, and each of the remaining doses includes about 200 mg of Compound 1, or a salt or neutral form thereof. In some embodiments, the dosing regimen consists of (a) intravenously administering a first dose of about 400 mg of a salt of Compound 1, or a neutral form thereof, (b) intravenously administering a second dose of about 200 mg of a salt of Compound 1, or a neutral form thereof, and (c) optionally intravenously administering a third dose of about 200 mg of a salt of Compound 1, or a neutral form thereof, wherein the first dose is administered on day 1, the second dose is administered on day 8, and the third dose, if administered, is administered on day 15.

In some methods, a salt of Compound 1, or a neutral form thereof is intravenously administered to a subject (e.g., a human) in two or more weekly doses (e.g., 2, 3, 4, 5, 6, 7, 8, 9, 10, 11, or 12 doses) of about 400 mg of a salt of Compound 1, or a neutral form thereof. In some embodiments, the dosing regimen consists of (a) intravenously administering a first dose of about 400 mg of a salt of Compound 1, or a neutral form thereof, (b) intravenously administering a second dose of about 400 mg of a salt of Compound 1, or a neutral form thereof, and (c) optionally intravenously administering a third dose of about 400 mg of a salt of Compound 1, or a neutral form thereof, wherein the first dose is administered on day 1, the second dose is administered on day 8, and the third dose, if administered, is administered on day 15.

In any of the methods described herein, the timing of the administration of a compound of any of formulas (I)-(III) (e.g., a salt of Compound 1, or a neutral form thereof) depends on the medical and health status of the subject (e.g., a human). In some embodiments, the subject is about to be immunocompromised by a disease, a medical procedure, a drug, and/or a pathogen. In some embodiments, the subject is already immunocompromised by a disease, a medical procedure, a drug, and/or a pathogen. For example, a subject who is about to undergo an immunosuppressive therapy may be administered a compound of any of formulas (I)-(III) (e.g., a salt of Compound 1, or a neutral form thereof) before, during, and/or after receiving the immunosuppresive therapy. The timing of the administration of a compound of any of formulas (I)-(III) (e.g., a salt of Compound 1, or a neutral form thereof) may be optimized by a physician to reduce the risk of or to treat a *Pneumocystis* infection in a subject (e.g., an immunocompromised subject).

The subject (e.g., a human) treated using the methods of the disclosure can be immunocompromised. The immune system of an immunocompromised subject may be weakened or compromised by a disease (e.g., an HIV infection, an autoimmune disease, cancer), a medical procedure (e.g., an organ transplant (e.g., a solid organ transplant) or a bone marrow transplant), a drug (e.g., an immunosuppressant), and/or a pathogen (e.g., bacteria, fungus, virus). In some embodiments, a subject (e.g., an immunocompromised subject) is about to have, is currently having, or has had a disease. In some embodiments, a subject (e.g., an immunocompromised subject) is about to undergo or has undergone a transplantation procedure (e.g., an organ transplant (e.g., a solid organ transplant) or a bone marrow transplant) or a radiation therapy. In some embodiments, a subject (e.g., an immunocompromised subject) is about to be administered, is currently administered, or has been administered one or more drugs that weaken the immune system, e.g., an immunosuppressant (e.g., a corticosteroid). In some embodiments, a subject (e.g., an immunocompromised subject) is about to undergo, is currently undergoing, or has undergone an immunosuppressive therapy, an anti-TNF therapy, a corticosteroid therapy, and/or a chemotherapy. In some embodiments, a subject's immune system is compromised by a pathogen (e.g., bacteria, fungus, virus), i.e., either the pathogen is currently present within the subject or had previously infected the subject. For example, the subject can be HIV positive, have hyper IgM syndrome, or have a $CD4^+$ T-cell count of less than 200 cells/μl of blood.

For the treatment of a subject undergoing an immunosuppression therapy, a compound of any of formulas (I)-(III) can be administered concurrently or within a few days (e.g., 1-15 days, e.g., 1, 2, 3, 4, 5, 6, 7, 8, 9, 10, 11, 12, 13, 14, or 15 days (e.g., 7 days)), before and/or after, the subject undergoes an immunosuppression therapy.

For the treatment of a subject undergoing an anti-TNF therapy, a corticosteroid therapy, or a chemotherapy a compound of any of formulas (I)-(III) can be administered concurrently or within a few days (e.g., 1-15 days, e.g., 1, 2, 3, 4, 5, 6, 7, 8, 9, 10, 11, 12, 13, 14, or 15 days (e.g., 7 days)), before and/or after, the subject undergoes an anti-TNF therapy, a corticosteroid therapy, or a chemotherapy.

For the treatment of a subject undergoing a transplantation procedure (e.g., an organ transplant (e.g., a solid organ transplant) or a bone marrow transplant), a compound of any of formulas (I)-(III) can be administered concurrently or within a few days (e.g., 1-15 days, e.g., 1, 2, 3, 4, 5, 6, 7, 8, 9, 10, 11, 12, 13, 14, or 15 days (e.g., 7 days)), before and/or after, the subject undergoes a transplantation procedure (e.g., an organ transplant (e.g., a solid organ transplant) or a bone marrow transplant). In some embodiments, the treatment may start before and continue after the organ transplant.

In any of the methods described herein, a second antifungal agent can be used in combination with a compound of any of formulas (I)-(III) (e.g., a salt form of Compound 1) to prevent or treat a *Pneumocystis* infection (e.g., a PCP infection). The second antifungal agent and the compound of any of formulas (I)-(III) can be administered concurrently. Alternatively, the compound of any of formulas (I)-(III) can be administered first, followed by administration of the second antifungal agent. In some embodiments, the second antifungal agent is administered first, followed by administering of the compound of any of formulas (I)-(III).

Examples of second antifungal agents that can be used in the combination therapies described herein include, but are not limited to, clindamycin (sold under the brand names CLEOCIN® and DALACIN®), trimethoprim (sold under the brand names PROLOPRIM®, MONOTRIM®, and TRIPRIM®), sulfamethoxazole (sold under the brand name GANTANOL®), cotrimoxazole (a combination of trimethoprim and sulfamethoxazole (aka TMP-SMX); this combination is sold under the brand names BACTRIM®, COTRIM®, SULFATRIM®, and SEPTRA®), atovaquone (sold under the brand name MEPRON®), pentamidine (sold under the brand names NEBUPENT® and PENTRAM®), primaquine, pyrimethamine (sold under the brand name DARAPRIM®), and pharmaceutically acceptable salts thereof.

Alternatively, the second antifungal agents that can be used in the combination therapies described herein is selected from glucan synthase inhibitors (e.g., echinocandins, enfumafungins), polyene compounds, azole compounds, and pharmaceutically acceptable salts thereof.

Examples of glucan synthase inhibitors that can be used in the combination therapies of the disclosure include, but are not limited to echinocandins (e.g., caspofungin, micafungin, or anidulafungin) enfumafungin (e.g., SCY-078 (aka MK-3118, see Lepak et al., Antimicrobial agents and chemotherapy 59:1265 (2015)), and pharmaceutically acceptable salts thereof.

The azole compounds are antifungal compounds that contain an azole group (i.e., a five-membered heterocyclic ring having at least one N and one or more heteroatoms selected from N, O, or S). Azole compounds function by binding to the enzyme 14α-demethylase and disrupt, inhibit, and/or prevent its natural function. The enzyme 14α-demethylase is a cytochrome P450 enzyme that catalyzes the removal of the C-14 α-methyl group from lanosterol before lanosterol is converted to ergosterol, an essential component in the fungal cell wall. Therefore, by inhibiting 14α-demethylase, the synthesis of ergosterol is inhibited. Examples of azole compounds that can be used in the combination therapies of the disclosure include, but are not limited to (e.g., VT-1161, VT-1129, VT-1598, fluconazole, albaconazole, bifonazole, butoconazole, clotrimazole, econazole, efinaconazole, fenticonazole, isavuconazole, isoconazole, itraconazole, ketoconazole, luliconazole, miconazole, omoconazole, oxiconazole, posaconazole, pramiconazole, ravuconazole, sertaconazole, sulconazole, terconazole, tioconazole, and voriconazole), VL-2397, and flucytosine (ANCOBON®).

Polyene compounds are compounds that insert into fungal membranes, bind to ergosterol and structurally related sterols in the fungal membrane, and disrupt membrane structure integrity, thus causing leakage of cellular components from a fungus that causes infection. Polyene compounds typically include large lactone rings with three to eight conjugated carbon-carbon double bonds and may also contain a sugar moiety and an aromatic moiety. Polyene compounds typically include large lactone rings with three to eight conjugated carbon-carbon double bonds and may also contain a sugar moiety and an aromatic moiety.

Examples of polyene compounds that can be used in the combination therapies of the disclosure include, but are not limited to, 67-121-A, 67-121-C, amphotericin B, derivatives of amphotericin B (e.g., C35deOAmB; see Gray et al., Proceedings of the National Academy of Sciences 109:2234 (2012)), arenomvcin B, aurenin, aureofungin A, aureotuscin, candidin, chinin, chitin synthesis inhibitors (e.g., lufenuron), demethoxyrapamycin, dermostatin A, dermostatin B, DJ-400-B$_1$, DJ-400-B$_2$, elizabethin, eurocidin A, eurocidin B, filipin I, filipin II, filipin III, filipin IV, fungichromin, gannibamycin, hamycin, levorin A$_2$, lienomycin, lucensomycin, mycoheptin, mycoticin A, mycoticin B, natamycin, nystatin A, nystatin A$_3$, partricin A, partricin B, perimycin A, pimaricin, polifungin B, rapamycin, rectilavendomvcin, rimocidin, roflamycoin, tetramycin A, tetramycin B, tetrin A, tetrin B, and pharmaceutically acceptable salts thereof.

The following Examples are intended to further illustrate but not to limit the disclosure herein.

EXAMPLES

Example 1—Efficacy of Compound 1 to Prevent *Pneumocystis* Murina Infection In Vivo The in vivo efficacy of Compound 1 in preventing *Pneumocystis* murina infection in immunocompromised mice was evaluated.

Compound 1 Preparation

Compound 1 (as its acetate salt) was added to a vehicle solution. Briefly, the vehicle was prepared by first adding 1% Tween 20 to sterile phosphate-buffered saline (PBS) and then adding DMSO for a 10% DMSO in 1% Tween 20 in sterile PBS solution. Vehicle was stored in the refrigerator and aliquots were allowed to warm to room temperature before mixing with Compound 1. Drug preparations were prepared by adding Compound 1 to vehicle based on drug dosages and an average mouse weight of 24 g. For the 20 mg/kg/d dose, the drug was dissolved in vehicle to a concentration of 2.4 mg/ml. The mice then received 0.48 mg in a 200 µl dose. The drug was stored at −20° C. until initiation of dosage. The drug was prepared fresh for every two days of dosing.

TABLE 1

*Pneumocystis murina (P. murina)* prophylaxis study design.

| Group | Drug | Dose | # of Animals |
|---|---|---|---|
| 1 | Negative Control | — | 10 |
| 2 | Compound 1 | 20 mg/kg/3×/wk | 10 |
| 3 | Compound 1 | 20 mg/kg/1×/wk | 10 |
| 4 | Compound 1 | 2 mg/kg/3×/wk | 10 |
| 5 | Compound 1 | 2 mg/kg/1×/wk | 10 |
| 6 | Compound 1 | 0.2 mg/kg/3×/wk | 10 |
| 7 | Compound 1 | 0.2 mg/kg/1×/wk | 10 |
| 8 | Compound 1 | 50/250 mg/kg/3×/wk | 10 |

Experimental Method

C3H/HeN mice (Charles River) were infected with *P. murina* by intranasal inoculation of *P. murina* organisms at 2×106/50 µl from our liquid nitrogen repository. Prior to inoculation, the *P. murina* organisms were pre-incubated overnight in RPMI 1640 medium supplemented with calf serum and antibiotics to eliminate any bacterial contamination. The immune systems of the mice were suppressed by the addition of dexamethasone at 4 mg/liter to acidified drinking water (sulfuric acid at 1 ml/liter). Acidification is used to prevent secondary microbial infections. The mice were divided into a negative control group (control steroid—C/S) (Group 1 in Table 1), positive control group (trimethoprim/sulfamethoxazole—TMP/SMX) (Group 8 in Table 1), and treatment groups (Groups 2-7 in Table 1). Drugs to be tested were administered intraperitoneally (i.p.) on a mg/kg/d basis; dose, route, and frequency of administration will vary depending on the agent being tested. For the prophylaxis study, Compound 1 was administered at the same time the mice were inoculated. Immune suppression and treatment continued for the entire 6-week study. No complications were noted during the course of this study. The mice tolerated the dosing regimen with no significant deaths observed. At the end of the study, the mice were euthanized by $CO_2$ and their lungs processed for analysis by homogenization. Slides were made from the lung homogenates at different dilutions and stained with Diff-Quik to quantify the trophic forms and cresyl echt violet to quantify the asci.

Calculations

Efficacy is based on the reduction of organism burden between the treatment groups and the negative control group as determined by microscopic evaluation. The nuclei and asci counts for each lung are log transformed and statistical analysis is determined by the analysis of variance (ANOVA); individual groups are compared by the Student-Newman-Keuls t test for multiple comparisons using GraphPad Prism. Statistical significance is accepted at a p value <0.05.

Results

Prophylactic treatment of *P. murina* infected mice with Compound 1 showed a statistically significant reduction in nuclei levels at all dose levels except for the 0.2 mg/kg/1×/week group as compared to the negative control group after 6 weeks of dosing (FIG. 1A). Three of the treatment groups (20 mg/kg/1×/week, 20 mg/kg/1×/week, and 2 mg/kg/3×/week groups) were equally as efficacious as the positive control TMP/SMX group with no nuclei seen by microscopic evaluation. All Compound 1 treatment groups showed a statistically significant reduction in asci levels compared to the negative control group (FIG. 1B) and there was no difference in efficacy between 5 treatment groups and the positive control TMP/SMX group with no asci observed by microscopic evaluation.

Example 2—Efficacy of Compound 1 to Treat *Pneumocystis* Murina Infection In Vivo The in vivo efficacy of Compound 1 in treating *Pneumocystis murina* infection in immunocompromised mice was evaluated.

Compound 1 Preparation

Compound 1 was added to a vehicle solution. Briefly, the vehicle was prepared by first adding 1% Tween 20 to sterile phosphate-buffered saline (PBS) and then adding DMSO for a 10% DMSO in 1% Tween 20 in sterile PBS solution. Vehicle was stored in the refrigerator and aliquots were allowed to warm to room temperature before mixing with Compound 1. Drug preparations were prepared by adding Compound 1 to vehicle based on drug dosages and an average mouse weight of 24 g. For the 20 mg/kg/d dose, the drug was dissolved in vehicle to a concentration of 2.4 mg/ml. The mice then received 0.48 mg in a 200 μl dose. The drug was stored at −20° C. until initiation of dosage. The drug was prepared fresh for every two days of dosing.

TABLE 2

*P. murina* treatment study design.

| Group | Drug | Dose | Treatment Days | # of Animals |
|---|---|---|---|---|
| 1 | Negative Control | — | 7 | 10 |
| 2 | Compound 1 | 20 mg/kg/d | 7 | 10 |
| 3 | Compound 1 | 2 mg/kg/d | 7 | 10 |
| 4 | Compound 1 | 0.2 mg/kg/d | 7 | 10 |
| 5 | TMP/SMX | 50/250 mg/kg/d | 7 | 8 |

Experimental Method

C3H/HeN mice (Charles River) were infected with *P. murina* pneumonia by intranasal inoculation of *P. murina* organisms from a liquid nitrogen repository at $2 \times 10^6/50$ μl. Prior to inoculation, the *P. murina* organisms were pre-incubated overnight in RPMI 1640 medium supplemented with calf serum and antibiotics to eliminate any bacterial contamination. The immune systems of the mice were suppressed by treatment with the anti-CD4$^+$ antibody GK 1.5. 300 μg of GK 1.5 was administered intraperitoneally 3× in week 1 prior to inoculating the mice. After inoculation, the GK 1.5 was administered 1×/week for remainder of the study. Mice were fed sterilized lab chow and supplied with acidified water (sulfuric acid at 1 ml/liter) to prevent secondary microbial infections.

After the mice developed a moderate infection level (approximately 5 weeks), they were divided into a negative control group (control steroid—C/S) (Group 1 in Table 2), positive control group (trimethoprim/sulfamethoxazole—TMP/SMX) (Group 5), and treatment groups (Groups 2-4). Drugs to be tested were administered intraperitoneally (i.p.) on a mg/kg/d basis for one week; dose, route, and frequency of administration varied depending on the agent being tested. The mice were euthanized by $CO_2$ at day 7. The mice were sacrificed and their lungs processed for analysis by homogenization. Slides were made from the lung homogenates at different dilutions and stained with Diff-Quik to quantify the trophic forms and cresyl echt violet to quantify the asci.

Calculations

Efficacy is based on the reduction of organism burden between the treatment groups and the negative control group as determined by microscopic evaluation. The nuclei and asci counts for each lung are log transformed and statistical analysis is determined by the analysis of variance (ANOVA); individual groups are compared by the Student-Newman-Keuls t test for multiple comparisons using GraphPad Prism v6. Statistical significance is accepted at a p value <0.05.

Results

Figures 2A, 2B:
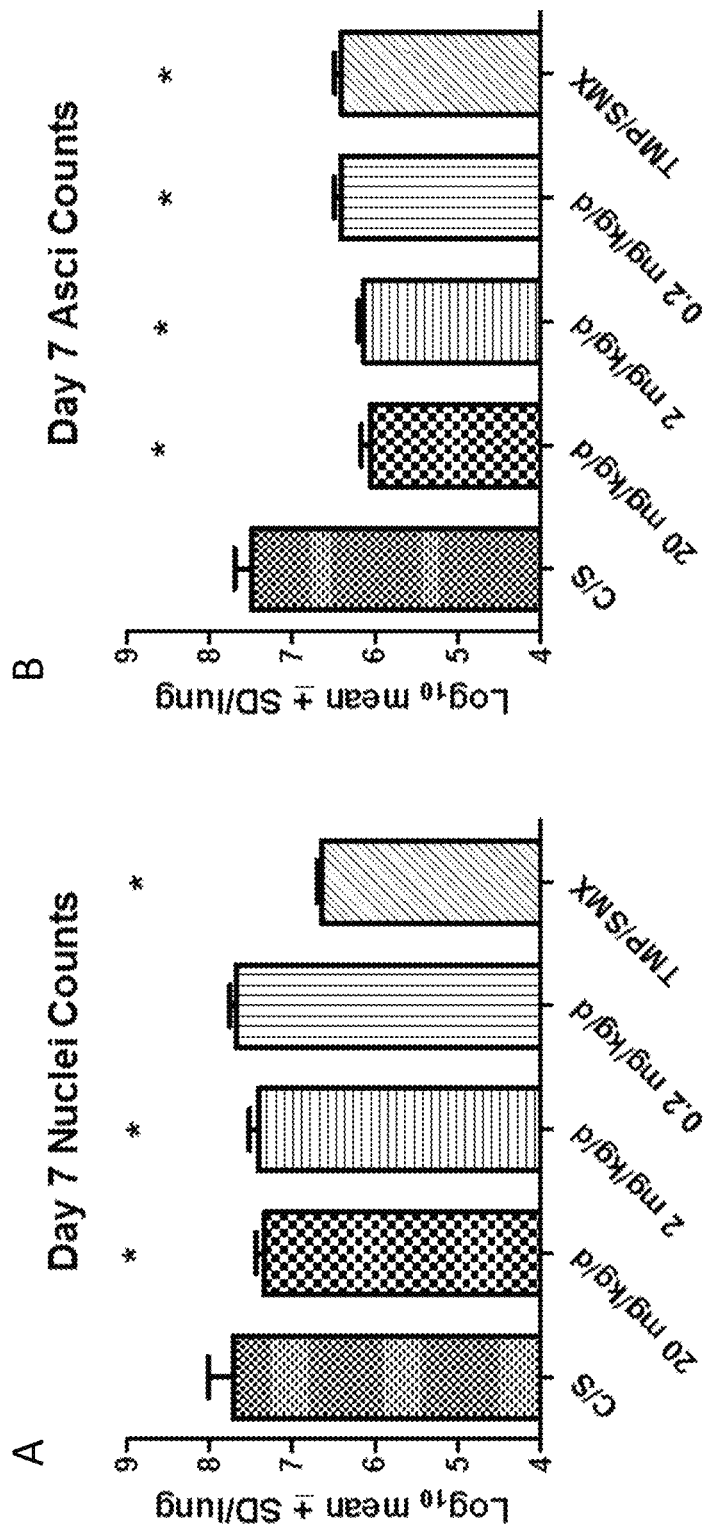
FIG. 2A shows the therapeutic effects of Compound 1 on lung burdens (shown as nuclei counts) in mice infected with *Pneumocystis* murina.
FIG. 2B shows the therapeutic effects of Compound 1 on lung burdens (shown as asci counts) in mice infected with *Pneumocystis* murina.

Treatment of *P. murina* infected mice with Compound 1 showed a statistically significant reduction in nuclei levels in the 20 mg/kg/d and 2 mg/kg/d treatment groups compared to the negative control group after 7 days of dosing (FIG. 2A). All Compound 1 treatment groups showed a statistically significant reduction in asci levels compared to the negative control group after 7 days (FIG. 2B) and there was no difference in efficacy between these 3 treatment groups and the positive control TMP/SMX group.

Example 3—Treatment of a *Pneumocystis* Pneumonia (PCP) in an Immunocompromised Subject An immunocompromised HIV positive human subject presenting with fever, cough, shortness of breath, weight loss, and/or night sweats is diagnosed with PCP using any one of a variety of methods (e.g., chest x-ray, gallium 67 scans). The diagnosis is confirmed by histological identification of the causative organism in sputum or bronchioalveolar lavage.

The subject commences treatment with 200-600 mg (e.g., 400 mg) of the acetate salt of Compound 1 intravenously administered once weekly for 2-12 weeks.

The CD4+ T-cell count of the subject is monitored as the subject undergoes anti-HIV treatment to strengthen the immune function of the subject.

Weekly treatment with compound 1 is continued until the CD4+ T-cell count of the subject reaches a predetermined level (e.g., greater than 600 cells/µl of blood).

Example 4—Prophylaxis Against *Pneumocystis* Pneumonia Infection in a Subject

A human subject is scheduled to undergo a kidney transplant. As part of that procedure, the subject receives an immunosuppressant to prevent the emergence of Graft-versus-host disease.

Seven days prior to commencing immunosuppression therapy, the subject commences treatment with 200-600 mg (e.g., 400 mg) of the acetate salt of Compound 1 intravenously administered once weekly for 2-12 weeks.

Weekly treatment with compound 1 is continued until the subject is weaned from the immunosuppressant, or until normal immune function is restored.

Example 5—Pharmacological Basis of Compound 1 Efficacy

Methods

Pharmacokinetic Study.

Healthy female ICR mice were given a single dose of Compound 1 via intraperitoneal (IP) injection. The following doses, at three mice per dose, were studied: 1, 4, and 16 mg/kg. Compound 1 plasma concentrations were determined at 0, 1, 3, 6, 12, 24, 48, 72, 96 hours post-dose using a validated LC/MS assay with a lower limit of quantification of 0.02 µg/mL.

Dose-Fractionation Study.

Male or female ICR mice (5 per regimen and observation time) weighing 22±2 g were rendered neutropenic for the study by injecting the mice with cyclophosphamide treatment four days (−Day 4) (150 mg/kg IP) and one day (−Day 1) prior to infection at 100 mg/kg IP. Neutropenia was sustained for the duration of the study with cyclophosphamide doses (100 mg/kg IP) every 48 hours on days +1, +3, +5 and +7 after infection. Each animal was inoculated intravenously with $1 \times 10^3$ CFU of *Candida albicans* (Strain R303, MIC=0.125 mg/L). Compound 1 (or vehicle) was administered 24 hours post-infection via IP injection. The doses studied are shown in Table 3.

TABLE 3

Summary of Compound 1 dosing regimens evaluated

| Total Dose | Dosing Interval | Fractionated Doses |
| --- | --- | --- |
| 0.7 mg/kg | Single Dose | 0.7 mg/kg × 1 |
| | Twice Weekly | 0.35 mg/kg × 2 |
| | Daily | 0.1 mg/kg × 7 |
| 2 mg/kg | Single Dose | 2 mg/kg × 1 |
| | Twice Weekly | 1 mg/kg × 2 |
| | Daily | 0.29 mg/kg × 7 |

TABLE 3-continued

Summary of Compound 1 dosing regimens evaluated

| Total Dose | Dosing Interval | Fractionated Doses |
| --- | --- | --- |
| 7 mg/kg | Single Dose | 7 mg/kg × 1 |
| | Twice Weekly | 3.5 mg/kg × 2 |
| | Daily | 1 mg/kg × 7 |

Mice were sacrificed 168 hours (7 days) following the start of treatment. Control arm mice were sacrificed 0, 24, and 48 hours post administration of vehicle. Paired kidneys are aseptically harvested, homogenized, and plated for colony counts to determine the fungal burden (CFU/g).

Pharmacokinetic-Pharmacodynamic Analyses.

Using the data collected from the PK study, a PK model was developed in S-ADAPT. Using the developed PK model, concentration-time profiles and $AUC_{0-168\ h}$ values were computed for each dosing regimen administered in the dose-fractionation study. Free-drug plasma concentrations were generated using a murine protein binding value of 99.1%. Relationships between the change in $\log_{10}$ CFU from start of therapy and $AUC_{0-168\ h}$ were explored.

Results

Compound 1 exhibited linear PK over the dose ranged studied (1 to 16 mg/kg IP). A 4-compartment model best described the PK data. Model fits are displayed in FIG. 4.

The results of the dose-fractionation study are displayed in FIG. 5, which shows that fungi grew well in the no-treatment control group. The magnitude of net change in fungal density ($\log_{10}$ CFU) was similar regardless of fractionation schedule within the Compound 1 0.7 and 7 mg/kg dosing groups. However, results within the Compound 1 2 mg/kg group varied by the fractionation schedule.

The change in $\log_{10}$ CFU reduction from baseline at 168 hours by fractionation schedule for the Compound 1 2 mg/kg group is displayed in FIG. 6. When a total dose of 2 mg/kg was delivered daily (0.29 mg/kg/day), the magnitude of net change in fungal density ($\log_{10}$ CFU) was similar to the no-treatment control group. However, when 2 mg/kg is delivered as a single dose, there was a greater than $2$-$\log_{10}$ CFU reduction from baseline at 168 hours. The 2 mg/kg×1 and 0.29 mg/kg daily×7 regimens had similar cumulative Compound 1 exposures at 168 hours, as displayed in FIG. 5. Despite having similar exposures, which influences efficacy, these regimens showed very different effects.

Free-drug plasma concentration-time profiles of the three fractionated Compound 1 2 mg/kg dosing regimens are displayed in FIG. 7. All three regimens display very different exposure profiles. In particular, the single dose regimen results in larger Compound 1 exposures early in therapy. Free-drug plasma $AUC_{0-24}$ is 0.0654, 0.0303, and 0.00948 mg·h/L following administration of Compound 1 2 mg/kg as a single dose, twice weekly, and daily regimen, respectively. Further, administration of a single dose results in free-drug plasma concentrations which remain above those for the twice weekly and daily regimens for 84 and 48 hours, respectively.

Three Compound 1 regimens with similar total exposures, yet very different exposure shapes, display considerably different efficacy. This suggests that the shape of the Compound 1 AUC is a determinant of efficacy, with front loaded regimens demonstrating greater efficacy. The magnitude of the net change in fungal burden was similar regardless of fractionation schedule within the Compound 1 0.7 and 7 mg/kg dosing groups, but differed within the 2 mg/kg group. A 2 mg/kg dose was considerably more effective when given once per week compared to the same dose divided into twice-weekly or daily regimens.

The invention claimed is:
1. A method of treating or reducing the risk of a *Pneumocystis* infection in a subject, the method comprising administering to the subject a pharmaceutical composition comprising the acetate salt of Compound 1:

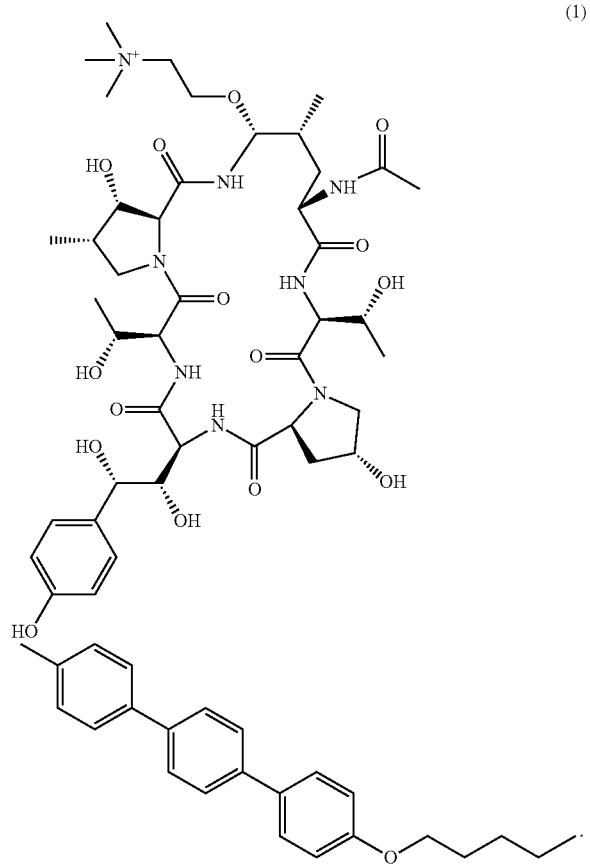

(1)

2. The method of claim 1, wherein the pharmaceutical composition comprises 150 mg to 800 mg of the acetate salt of Compound 1.
3. The method of claim 1, wherein the treating reduces the cyst burden in the lung of the subject.
4. The method of claim 1, wherein the treating comprises inhibiting the reproduction of a *Pneumocystis* spp. in the subject.
5. The method of claim 1, wherein the subject has *Pneumocystis* pneumonia.
6. The method of claim 1, wherein the subject is immunocompromised.
7. The method of claim 6, wherein the subject is HIV positive or has hyper IgM syndrome.
8. The method of claim 6, wherein the subject has a $CD4^+$ T-cell count of less than 200 cells/µl of blood.
9. The method of claim 6, wherein the pharmaceutical composition is administered concurrently or within 7 days, before and/or after, the subject undergoes an immunosuppression therapy, an anti-TNF therapy, a corticosteroid therapy, a chemotherapy, or a transplantation procedure.
10. The method of claim 1, wherein the subject is a human and the *Pneumocystis* infection is caused by *Pneumocystis jirovecii*.
11. The method of claim 1, wherein the pharmaceutical composition is administered intravenously.
12. The method of claim 1, wherein the pharmaceutical composition is administered subcutaneously.
13. The method of claim 2, wherein the pharmaceutical composition is administered intravenously.
14. The method of claim 2, wherein the pharmaceutical composition is administered subcutaneously.
15. The method of claim 1, wherein the pharmaceutical composition is administered concurrently with a second antifungal agent.
16. The method of claim 15, wherein the second antifungal agent is clindamycin, trimethoprim, sulfamethoxazole, cotrimoxazole, atovaquone, pentamidine, primaquine, pyrimethamine, or a pharmaceutically acceptable salt thereof.
17. The method of claim 15, wherein the second antifungal agent is selected from a glucan synthase inhibitor, a polyene compound, an azole compound, or a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 10,780,144 B2 | Page 1 of 2 |
| APPLICATION NO. | : 16/529390 | |
| DATED | : September 22, 2020 | |
| INVENTOR(S) | : Kenneth Bartizal et al. | |

It is certified that error appears in the above-identified patent and that said Letters Patent is hereby corrected as shown below:

On the Title Page

Page 2, under Foreign Patent Documents, in WO-2018/014333, replace "WO-2018/014333" with --WO-2019/014333--.

In the Specification

Column 3, Line 32, replace "Z" with --$Z_1$--.

Column 5, Line 5, replace " 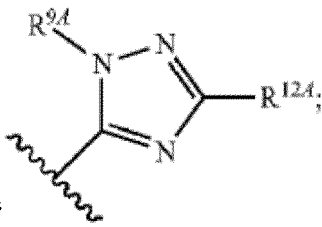 " with -- 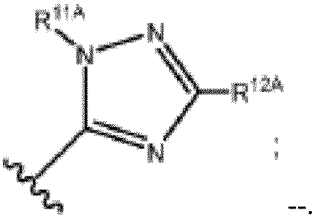 --.

Column 17, Line 35, replace " 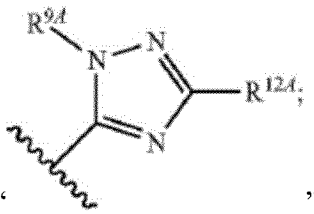 " with -- 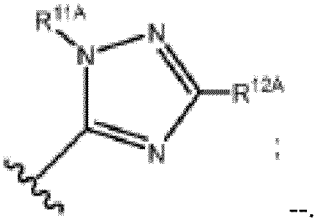 --.

Signed and Sealed this
Sixth Day of February, 2024

Katherine Kelly Vidal
*Director of the United States Patent and Trademark Office*

CERTIFICATE OF CORRECTION (continued)
U.S. Pat. No. 10,780,144 B2

Page 2 of 2

In the Claims

Column 31, Lines 10-40, replace " 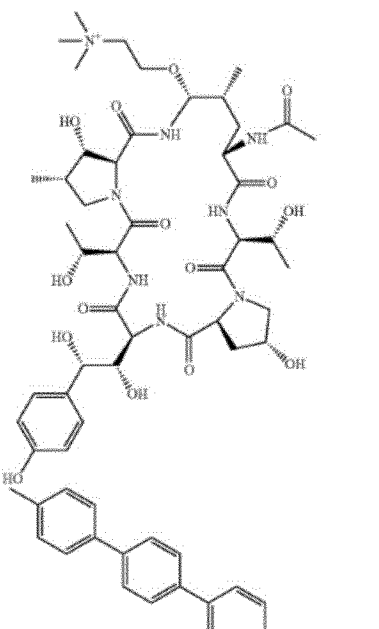 " with

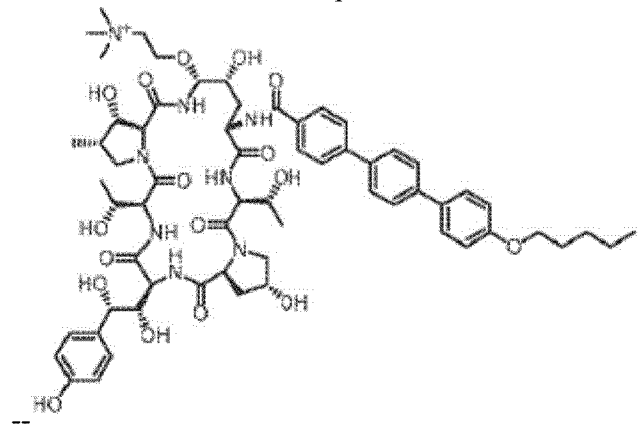 --.